(12) United States Patent
Ghosh

(10) Patent No.: US 10,858,371 B2
(45) Date of Patent: Dec. 8, 2020

(54) ANTI-CANCER AGENTS AND PREPARATION THEREOF

(71) Applicant: Purdue Research Foundation, West Lafayette, IN (US)

(72) Inventor: Arun K. Ghosh, West Lafayette, IN (US)

(73) Assignee: Purdue Research Foundation, West Lafayette, IN (US)

(*) Notice: Subject to any disclaimer, the term of this patent is extended or adjusted under 35 U.S.C. 154(b) by 0 days.

(21) Appl. No.: 16/335,378

(22) PCT Filed: Sep. 22, 2017

(86) PCT No.: PCT/US2017/052967
§ 371 (c)(1),
(2) Date: Mar. 21, 2019

(87) PCT Pub. No.: WO2018/057897
PCT Pub. Date: Mar. 29, 2018

(65) Prior Publication Data
US 2019/0218228 A1    Jul. 18, 2019

Related U.S. Application Data

(60) Provisional application No. 62/398,783, filed on Sep. 23, 2016.

(51) Int. Cl.
| | | |
|---|---|---|
| *C07D 493/10* | (2006.01) | |
| *C07D 309/14* | (2006.01) | |
| *A61K 31/35* | (2006.01) | |
| *A61K 31/357* | (2006.01) | |
| *A61K 31/351* | (2006.01) | |
| *A61K 31/695* | (2006.01) | |
| *A61K 31/4025* | (2006.01) | |
| *A61K 45/06* | (2006.01) | |

(52) U.S. Cl.
CPC ............ *C07D 493/10* (2013.01); *A61K 31/35* (2013.01); *A61K 31/351* (2013.01); *A61K 31/357* (2013.01); *A61K 31/4025* (2013.01); *A61K 31/695* (2013.01); *A61K 45/06* (2013.01); *C07D 309/14* (2013.01)

(58) Field of Classification Search
CPC .... C07D 493/10; C07D 309/14; A61K 31/35; A61K 31/357; A61K 31/351; A61K 31/695; A61K 31/4025; A61K 45/06; A61P 35/00
See application file for complete search history.

(56) References Cited

U.S. PATENT DOCUMENTS 8,969,405 B2 * 3/2015 Webb ............... C07D 493/10
514/452
2014/0134193 A1  5/2014  Subramanyam et al.
2015/0025017 A1  1/2015  Hubert et al.

FOREIGN PATENT DOCUMENTS

| CN | 109862916 A | 6/2019 | |
|---|---|---|---|
| IN | 201917015938 A | 8/2019 | |
| JP | 2019529563 A | 10/2019 | |
| MX | MX/A/2019/003368 | 9/2019 | |
| WO | WO-2015077370 A1 | 5/2015 | |
| WO | WO-2017214423 A2 * | 12/2017 | ........... C07D 309/28 |
| WO | WO-2018057897 A1 | 3/2018 | |

OTHER PUBLICATIONS

Osman, S., "Evaluation of FR901464 analogues in vitro and in vivo." MedChemComm 2.1 (2011): 38-43.*
Ghosh, A.K., "Enantioselective total syntheses of FR901464 and spliceostatin A and evaluation of splicing activity of key derivatives." The Journal of organic chemistry 79.12 (2014): 5697-5709.*
"International Application Serial No. PCT/US2017/052967, International Search Report dated Dec. 8, 2017", 3 pgs.
"International Application Serial No. PCT/US2017/052967, Written Opinion dated Dec. 8, 2017", 6 pgs.
Ghosh, Arun K, et al., "Enantioselective Syntheses of FR901464 and Spliceostatin A: Potent Inhibitors of Spliceosome", Org. Lett., vol. 15, No. 19, (Sep. 19, 2013), 5088-5091 pgs.
He, et al., "Cytotoxic Spliceostatins from *Burkholderia* sp. and Their Semisynthetic Analogues", J Nat Prod., (2014).
"European Application Serial No. 17853991.2, Response to Communication pursuant to Rule 161(2) & 162 EPC filed Nov. 18, 2019", 9 pgs.
"International Application Serial No. PCT/US2017/052967, International Preliminary Report on Patentability dated Apr. 4, 2019", 8 pgs.
"Chinese Application Serial No. 201780065546.7, Voluntary Amendment filed Jan. 3, 2020", w/ English Claims, 26 pgs.
"European Application Serial No. 17853991.2, Extended European Search Report dated Mar. 5, 2020", 7 pgs.

* cited by examiner

*Primary Examiner* — John M Mauro

(74) *Attorney, Agent, or Firm* — Schwegman Lundberg & Woessner, P.A.

(57) ABSTRACT

Embodiments provide, among other compounds, a family of compounds that can be used as therapeutic anti-cancer agents, methods for using such compounds to treat cancer, and methods of making such compounds.

18 Claims, No Drawings

ANTI-CANCER AGENTS AND PREPARATION THEREOF

CROSS-REFERENCE TO RELATED APPLICATIONS

This application is a U.S. National Stage Filing under 35 U.S.C. § 371 from International Application No. PCT/US2017/052967, filed Sep. 22, 2017, and published as WO 2018/057897 A1 on Mar. 29, 2018, which claims the benefit of U.S. Provisional Application Ser. No. 62/398,783, filed Sep. 23, 2016, which application is incorporated by reference as if fully set forth herein.

STATEMENT OF U.S. GOVERNMENT SUPPORT

This invention was made with government support under GM053386 awarded by the National Institutes of Health. The government has certain rights in the invention.

BACKGROUND

The American Cancer Society estimates that cancer costs the U.S. economy almost $200 billion per year due to the costs of medical treatment (about $80 billion per year) and lost productivity due to death and/or disability (about $120 billion per year). Of course, there is also a human toll as loved ones are diagnosed, treated, and sometimes die from many forms of cancer. Because of the high social and economic costs of cancer, new cancer treatments are a top priority for institutions such as the U.S. National Institutes of Health, as well as major pharmaceutical companies.

DESCRIPTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Proliferative diseases, such as cancer, cause harm to the body with the rapid growth of cells that interfere with the health function of nearby (or far-away) tissues. Because the cells replicate quickly, compounds that disrupt transcription pathways are valuable in fighting the disease. That is, if it is possible to disrupt the function of one or more proteins that play a role in a transcription pathway, the proliferation (and potential metastasis) of cancerous cells will be limited. Such a disruption would at least help a patient gain additional months or years of life.

One family of protein complexes involved in transcription pathways are spliceosomes. Spliceosomes typically include over 100 proteins that work together to control the excision of exons (i.e., splicing of introns) from genomic material during the transcription. Compounds that interfere with the function of spliceosomes or a spliceosome-regulation protein are valuable for slowing or stopping the spread of proliferative disease.

Embodiments include compounds that are effective at limiting the growth of proliferative cells and useful as therapeutic cancer agents. Embodiments also include compositions comprising these compounds as well as pro-drugs that result in the compounds when administered to a patient. The compounds are useful for the treatment of cancer, in particular solid tumor cell cancers, such as breast, lung, cervical, prostate, ovarian, pancreatic, and renal cell cancer. The compounds, compositions, and prodrugs can be administered to a patient in need of treatment for proliferative disease, e.g., cancer.

Embodiments additionally include methods of making the therapeutic compounds of the various embodiments described herein.

Various embodiments are directed to compounds having Formula I and stereoisomers, pharmaceutically acceptable salts, prodrugs (e.g., ester) or antibody conjugates (see, e.g., U.S. Pat. No. 8,663,643, which is incorporated by reference as if fully set forth herein) thereof:

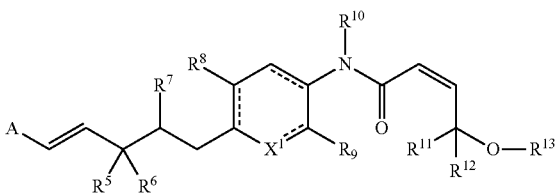

I wherein
the dashed lines in the ring comprising $X^1$ are double or single bonds;
$X^1$ is selected from the group consisting of CH and N if $X^1$ is doubly bonded to an adjacent carbon atom; or
$X^1$ is selected from the group consisting of O, $CH_2$, and NH if $X^1$ is singly bonded to an adjacent carbon atom;
A is selected from the group consisting of groups $A^1$-$A^5$:

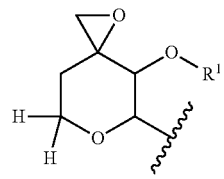

$A^1$

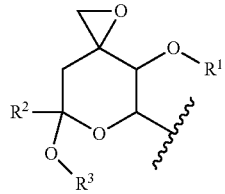

$A^2$

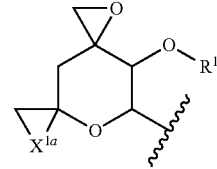

$A^3$

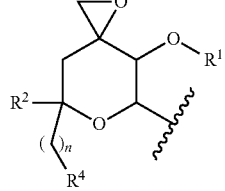

$A^4$

-continued

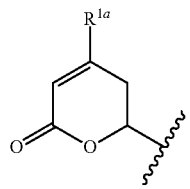

n is an integer from 1 to 10 (e.g., from 1 to 5; from 1 to 3; or from 2 to 5);
$X^{1a}$ is —$(CH_2)_g$—$X^{1b}$—, wherein g is an integer from 1 to 5 and $X^{1b}$ is a bond, O or $NR^{1a}$, wherein $R^{1a}$ is H or alkyl;
$R^1$ is selected from the group consisting of H, a hydroxyl protecting group, and alkyl;
$R^2$, $R^3$, $R^5$, and $R^8$-$R^{12}$ are each independently selected from the group consisting of H and alkyl;
$R^4$ is selected from the group consisting of —$N_3$, alkyl, aryl, heteroaryl, alkyl-$X^2$, and arylalkyl-$X^2$—, wherein $X^2$ is —O— or NH, or $R^4$ is —$C(O)R^{14}$, wherein $R^{14}$ is selected from the group consisting of H, —OH, alkyl-O—, and —$N(R^{15})_2$, wherein each $R^{15}$ is independently selected from the group consisting of H and alkyl;
$R^6$ and $R^7$, together, form a double bond or a cycloalkyl group; and
$R^{13}$ is selected from the group consisting of H, alkyl, and —$C(O)R^{16}$, wherein $R^{16}$ is selected from the group consisting of H, —OH, alkyl, alkyl-O—, and —$NR^{17}R^{18}$, wherein $R^{17}$ and $R^{18}$ are each independently selected from the group consisting of H and alkyl or $R^{17}$ and $R^{18}$ together with the nitrogen atom to which they are bound, form a 5- to 6-membered heterocyclic ring.

Various other embodiments are directed to compounds having Formulae Ia-Ic and stereoisomers, pharmaceutically acceptable salts, prodrugs (e.g., ester) or antibody conjugates thereof:

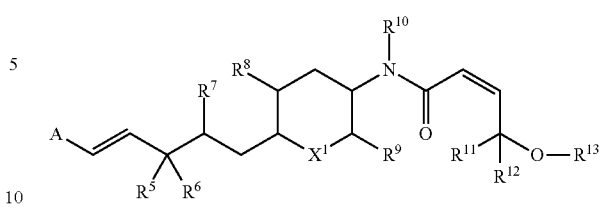

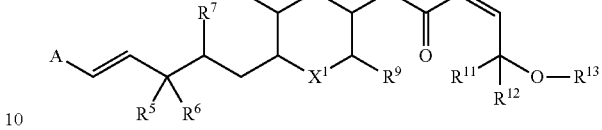

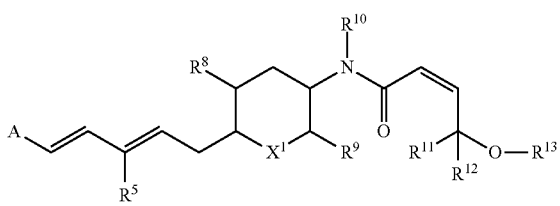

wherein A and $R^5$-$R^{13}$ are defined herein. In some embodiments, $X^1$ is O.

Various other embodiments are directed to compounds of the Formulae I and Ia-Ic wherein $R^{13}$ is —$C(O)R^{16}$. In some embodiments, $R^{16}$ is alkyl or —$NR^{17}R^{18}$. In some embodiments, $R^{16}$ is —$NR^{17}R^{18}$. In some embodiments, $R^{17}$ and $R^{18}$ together with the nitrogen atom to which they are bound, form a 5- to 6-membered heterocyclic ring.

Compounds encompassed by one or more of the Formulae I and Ia-Ic are compounds of the formulae:

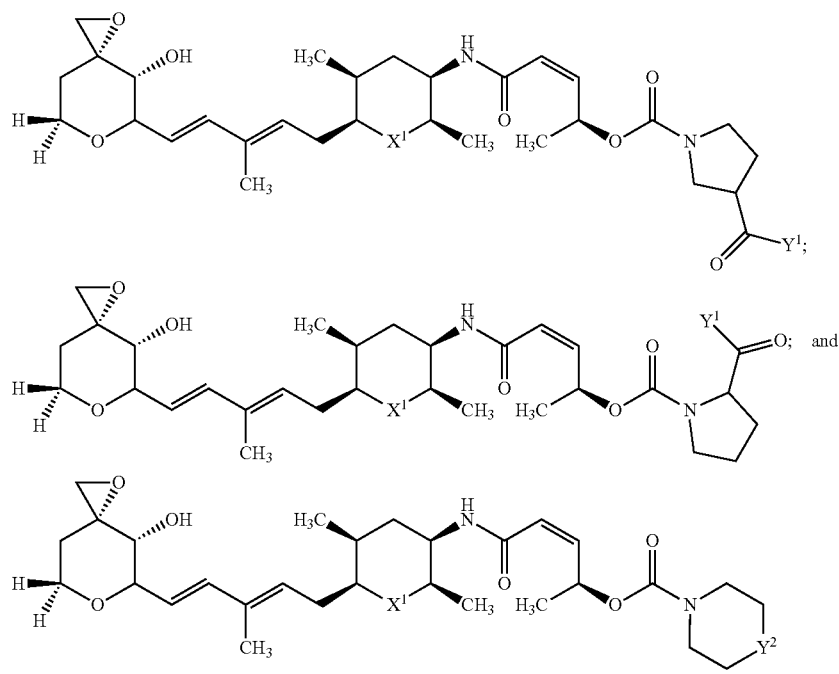

wherein $X^1$ is defined herein; $Y^1$ is selected from the group consisting of —OH, alkyl, alkyl-O—, and —NR$^{17}$R$^{18}$, wherein $R^{17}$ and $R^{18}$ are defined herein; and $Y^2$ is nothing, such that the heterocyclic ring is a 5-membered heterocyclic ring, O, CH$_2$ or NR$^{19}$, wherein $R^{19}$ is H or alkyl; and stereoisomers, pharmaceutically acceptable salts, prodrugs (e.g., ester) or antibody conjugates thereof. In some embodiments, $X^1$ is O.

Compounds encompassed by one or more of the Formulae I and Ia-Ic are also compounds of the formulae:

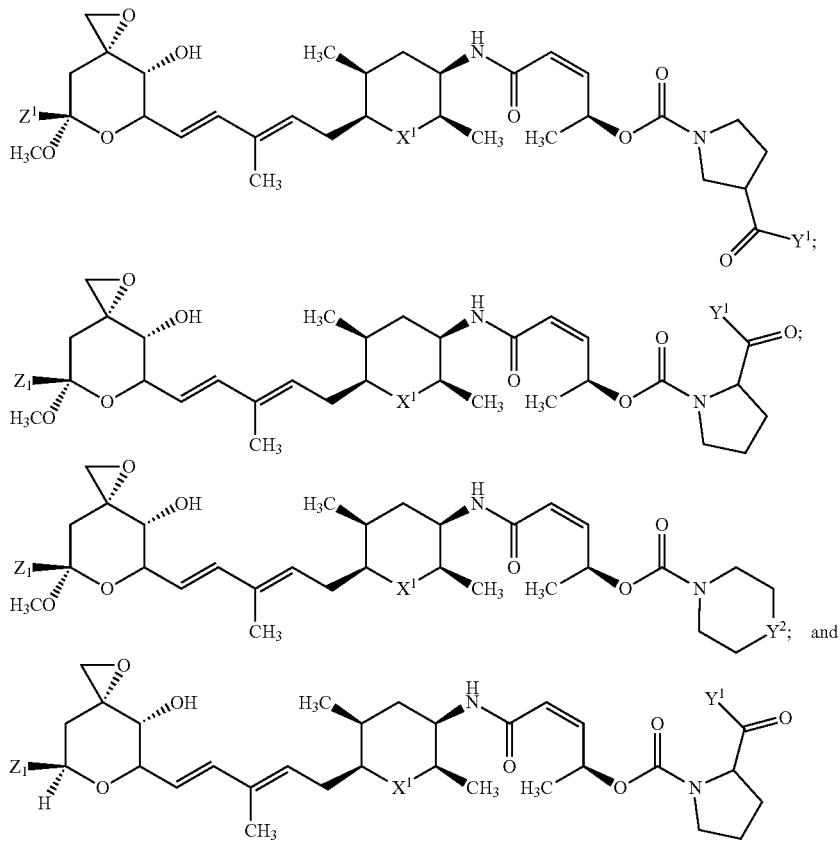

wherein $X^1$, $Y^1$, and $Y^2$ are defined herein; and $Z^1$ is H or alkyl; and stereoisomers, pharmaceutically acceptable salts, prodrugs (e.g., ester) or antibody conjugates thereof. In some embodiments, $X^1$ is O.

Still other compounds encompassed by one or more of the Formulae I and Ia-Ic are compounds of the formulae:

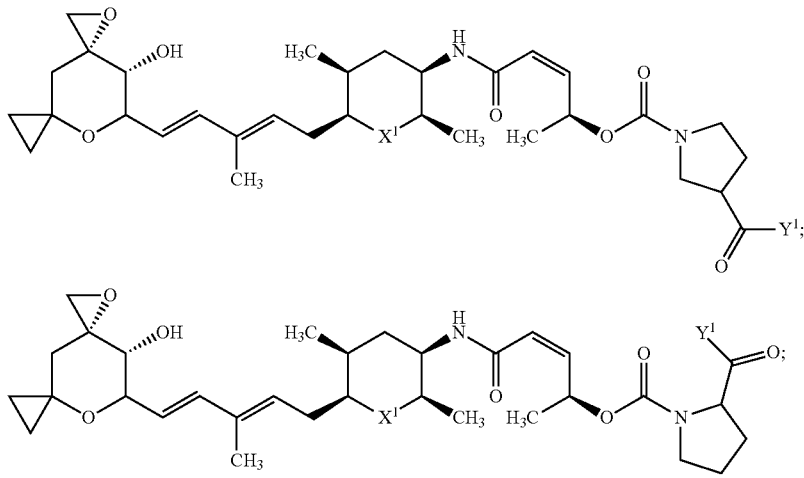

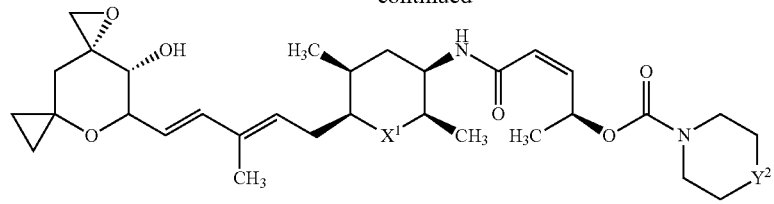

wherein $X^1$, $Y^1$, and $Y^2$ are defined herein; and stereoisomers, pharmaceutically acceptable salts, prodrugs (e.g., ester) or antibody conjugates thereof. In some embodiments, $X^1$ is O.

Yet other compounds encompassed by one or more of the Formulae I and Ia-Ic are compounds of the formulae:

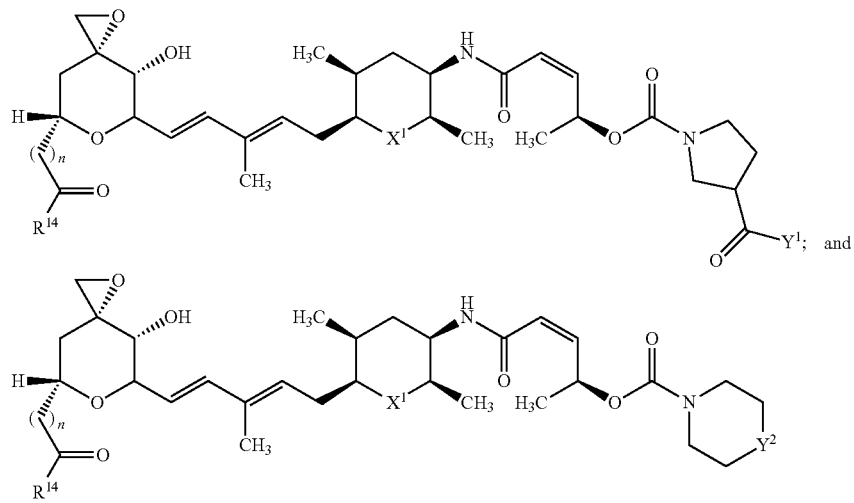

wherein n, $R^{14}$, $X^1$, $Y^1$, and $Y^2$ are defined herein; and stereoisomers, pharmaceutically acceptable salts, prodrugs (e.g., ester) or antibody conjugates thereof. In some embodiments, $X^1$ is O.

Other compounds encompassed by one or more of the Formulae I and Ia-Ic are compounds of the formulae:

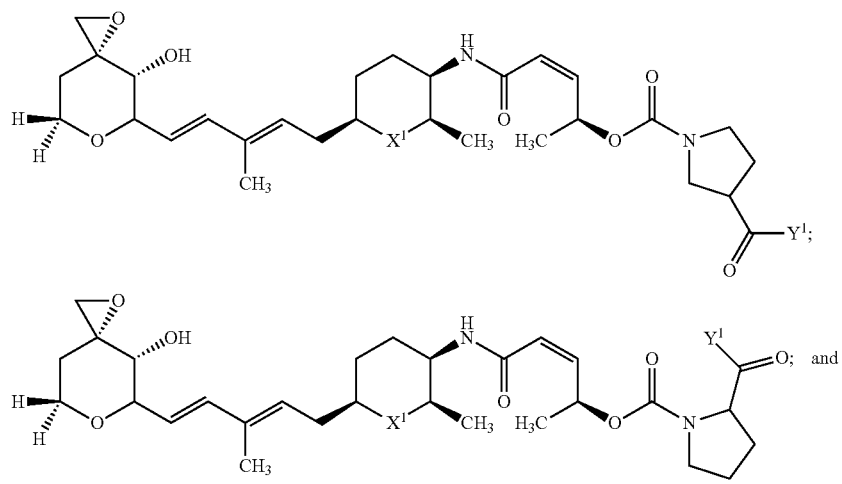

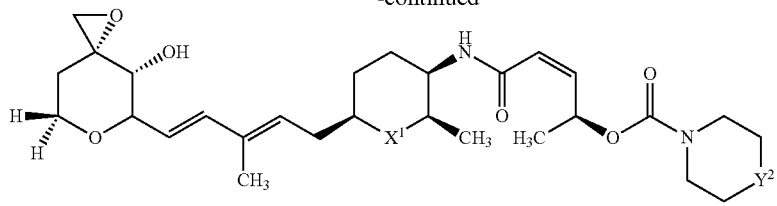
wherein $X^1$, $Y^1$, and $Y^2$ are defined herein; and stereoisomers, pharmaceutically acceptable salts, prodrugs (e.g., ester) or antibody conjugates thereof. In some embodiments, $X^1$ is O.
Compounds encompassed by one or more of the Formulae I and Ia-Ic are compounds of the formulae:
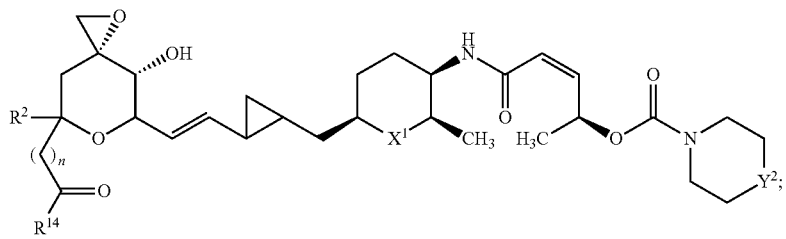
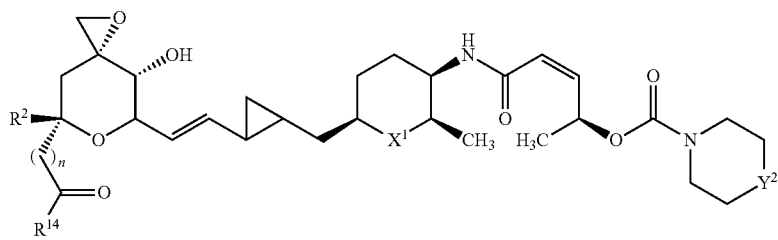
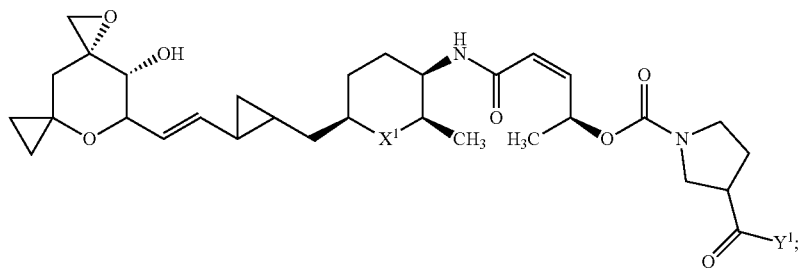
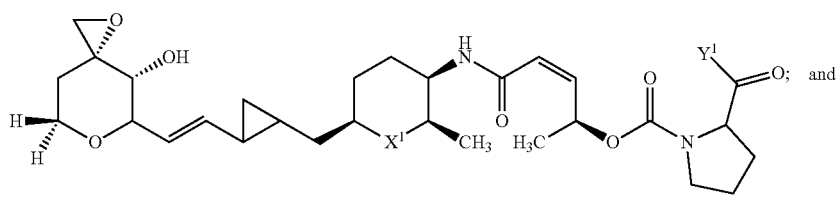
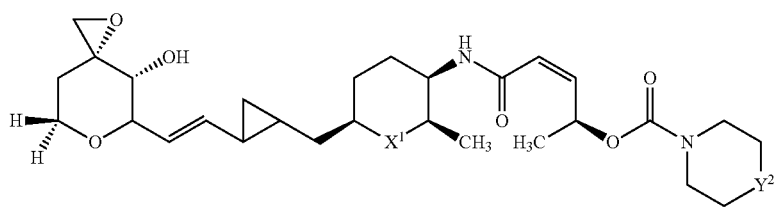

wherein n, $R^2$, $R^{14}$, $X^1$, $Y^1$, and $Y^2$ are defined herein; and stereoisomers, pharmaceutically acceptable salts, prodrugs (e.g., ester) or antibody conjugates thereof. In some embodiments, $X^1$ is O.

Compounds encompassed by one or more of the Formulae I and Ia-Ic are compounds of the formulae:

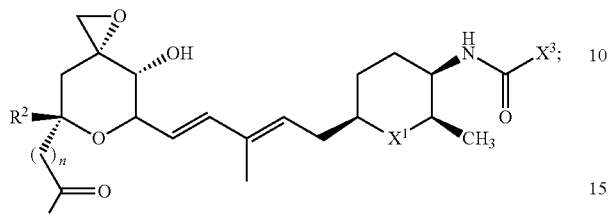

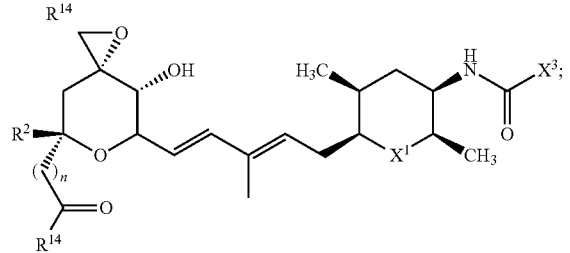

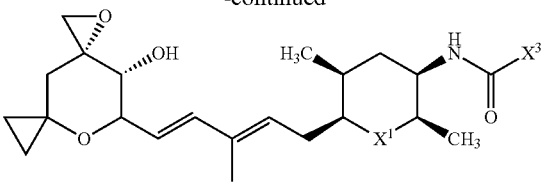

-continued wherein n, $R^2$, $R^{14}$, $X^1$, and $Y^1$ are defined herein; $X^3$ is selected from the group consisting of alkyl, aryl, and $R^{20}$—O—, wherein $R^{20}$ is selected from the group consisting of alkyl, cycloalkyl, and heterocyclyl; and stereoisomers, pharmaceutically acceptable salts, prodrugs (e.g., ester) or antibody conjugates thereof. In some embodiments, $X^1$ is O.

Compounds encompassed by one or more of the Formulae I and Ia-Ic are compounds of the formulae:

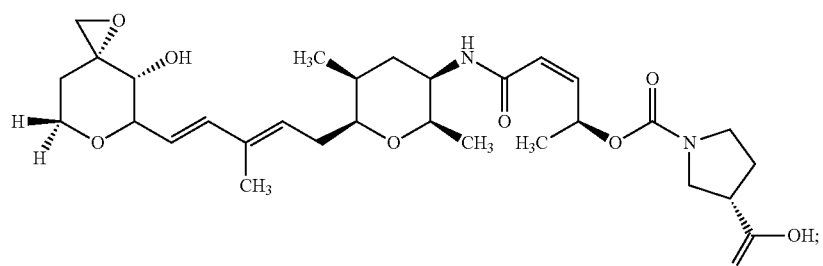

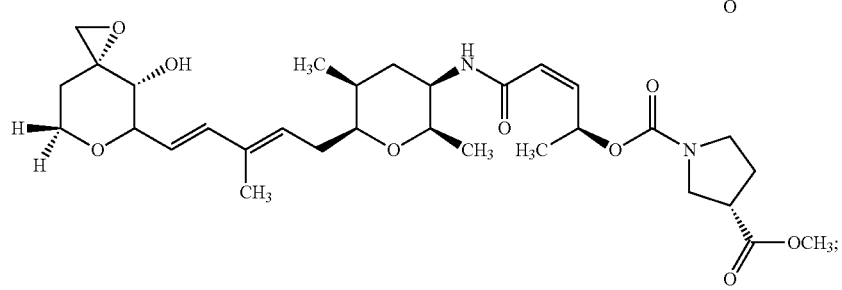

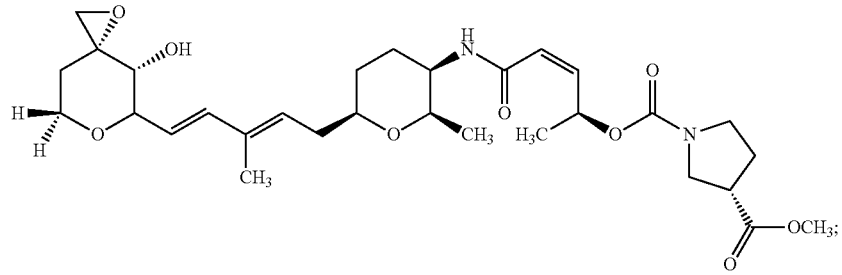

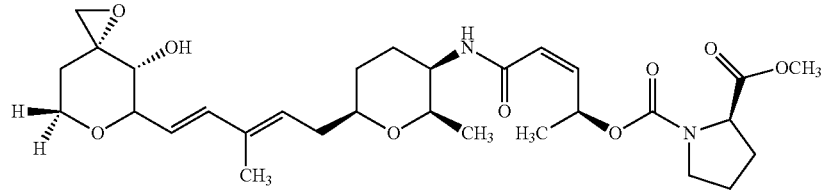

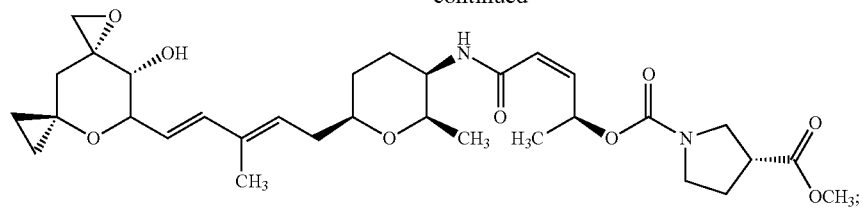

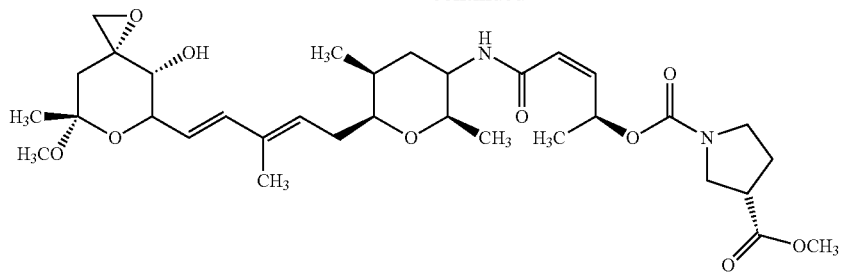
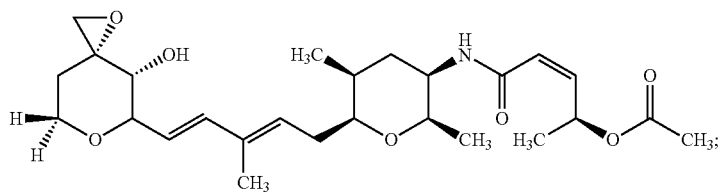
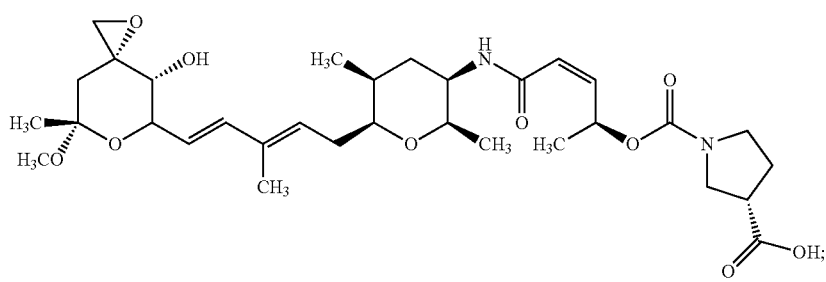
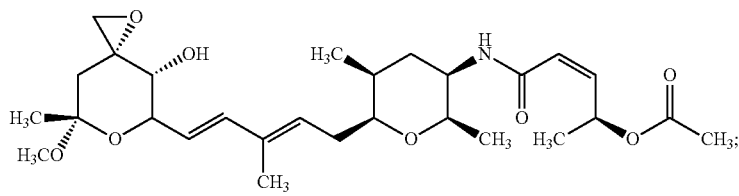
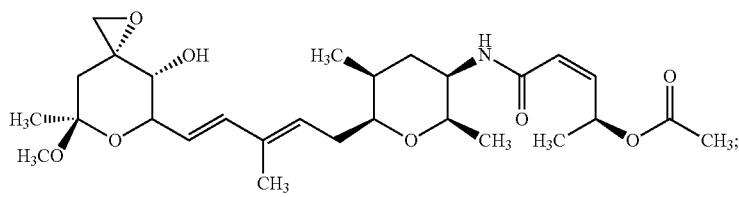
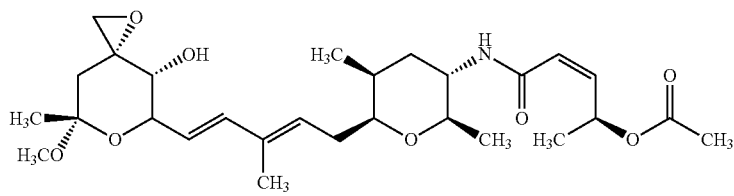
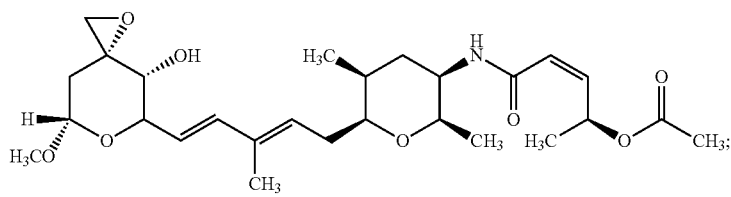
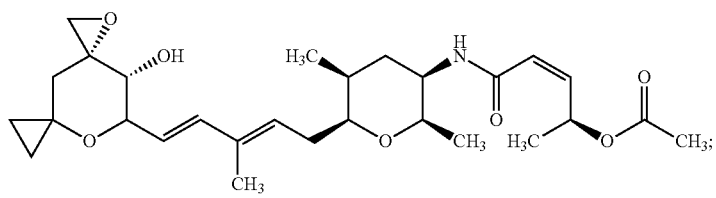

-continued
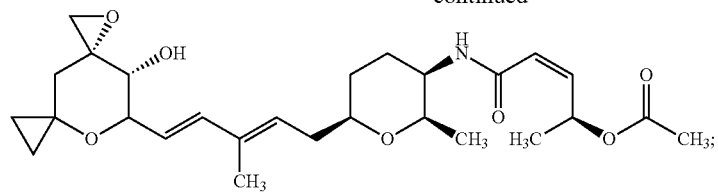
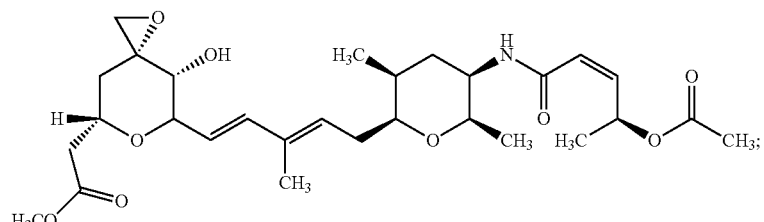
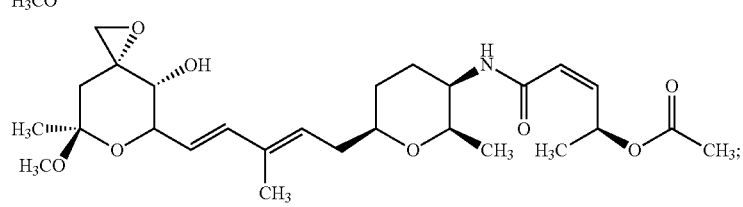
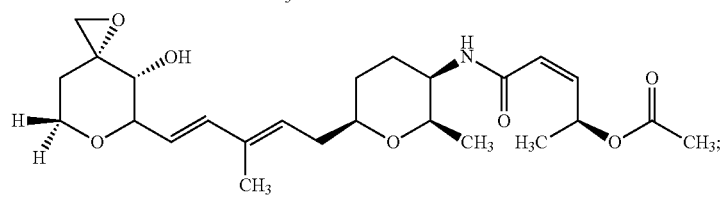
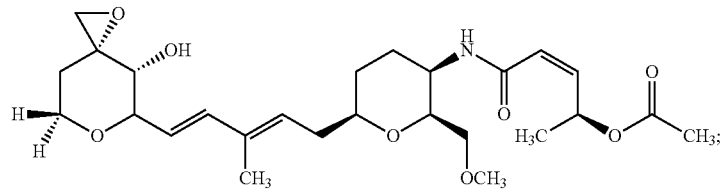
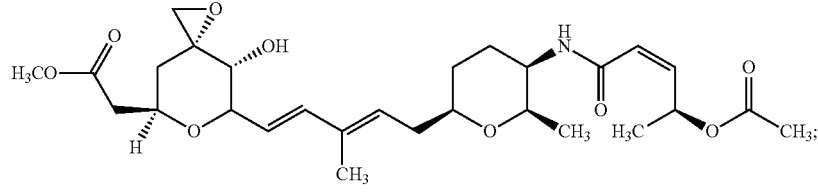
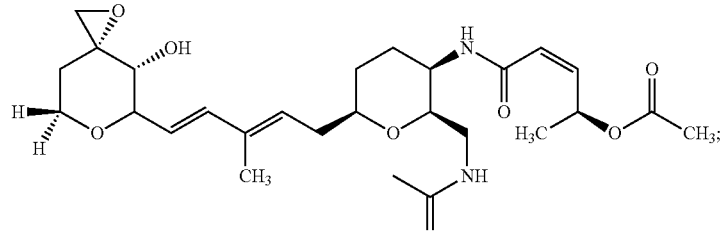
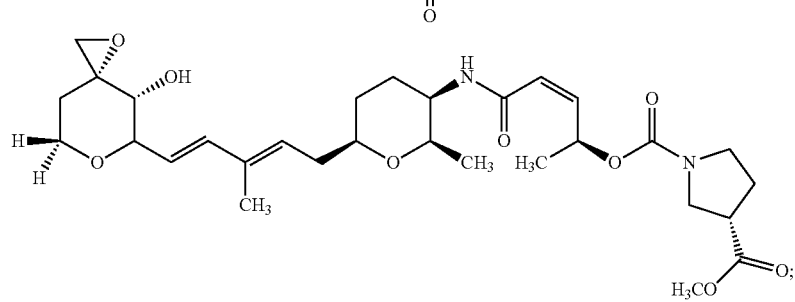

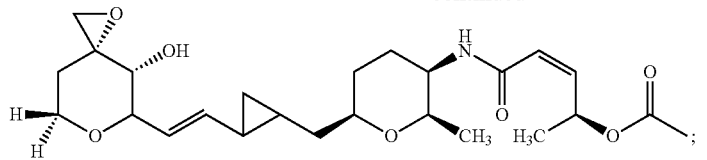
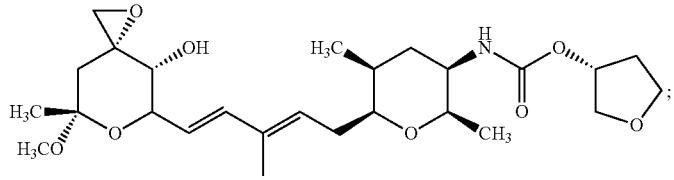
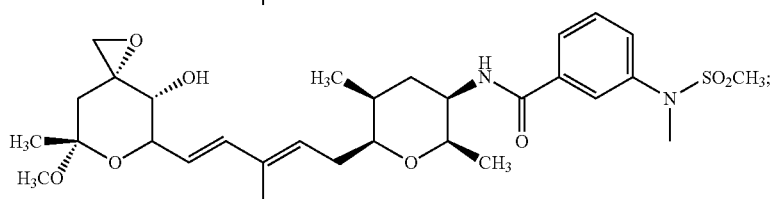
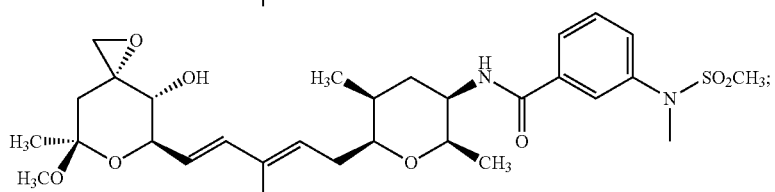
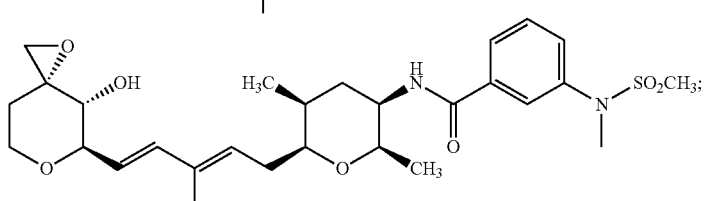
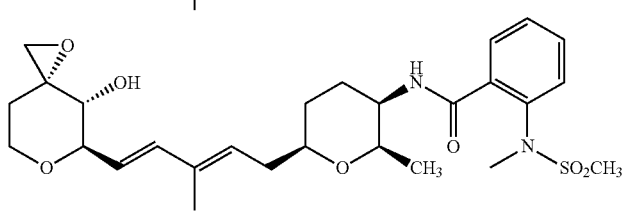
and stereoisomers, pharmaceutically acceptable salts, prodrugs (e.g., ester) or antibody conjugates thereof.
Compounds encompassed by one or more of the Formulae I and Ia-Ic are compounds of the formulae:
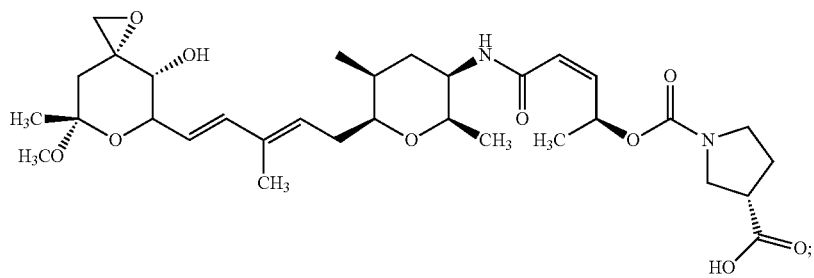

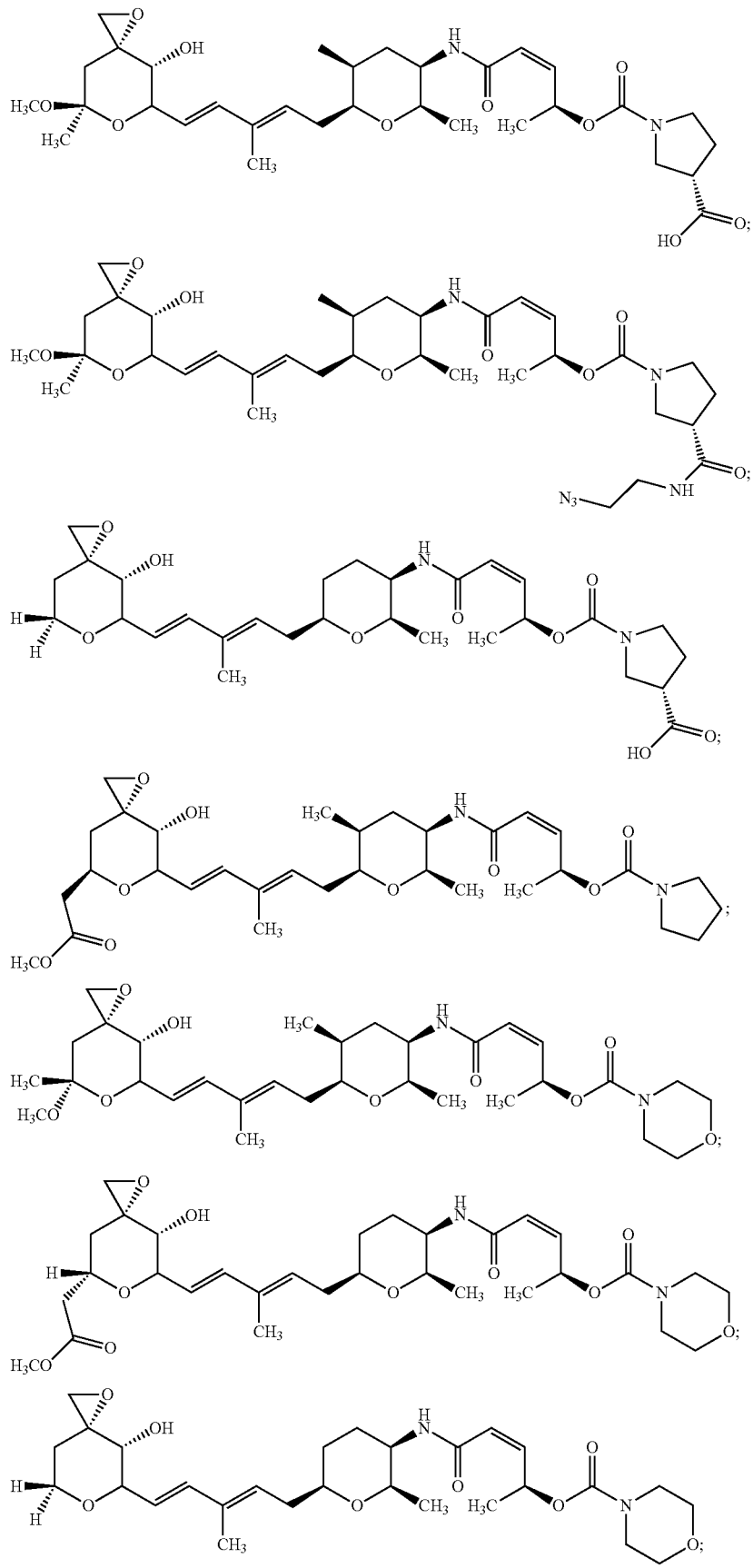

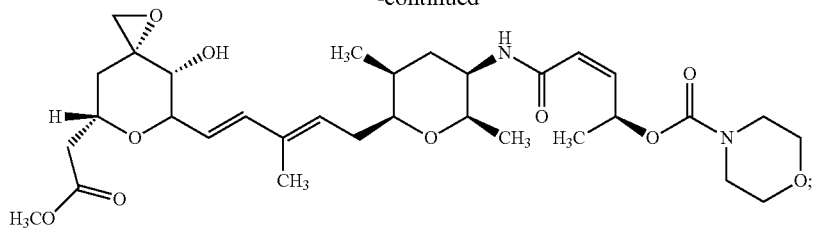
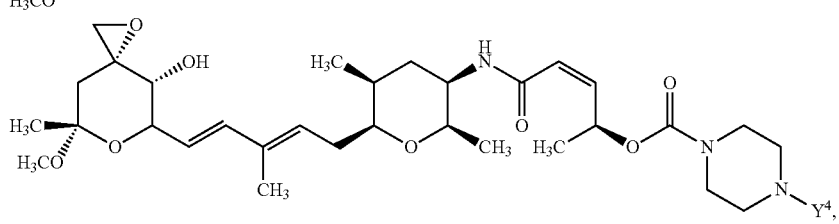
wherein $Y^4$ is a protecting group, such as a t-butyloxycarbonyl (BOC) group or a fluorenylmethyloxycarbonyl (FMOC) group;
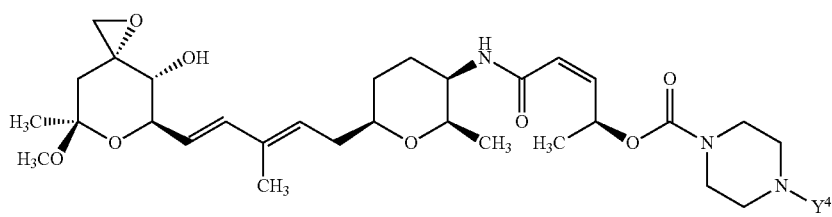
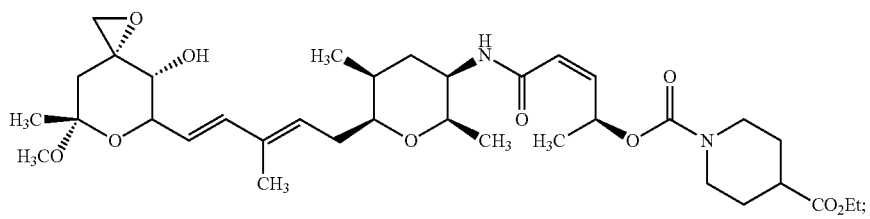
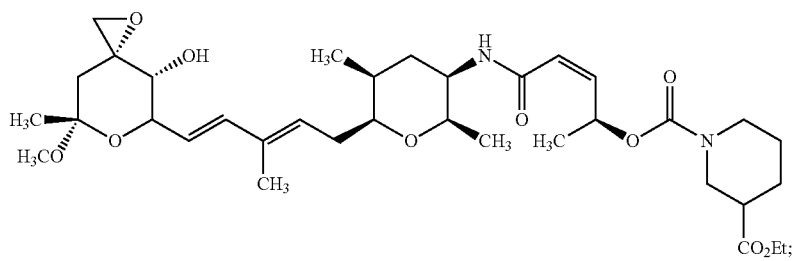
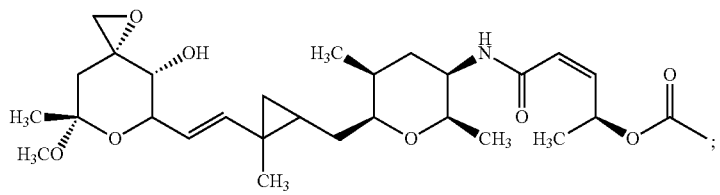
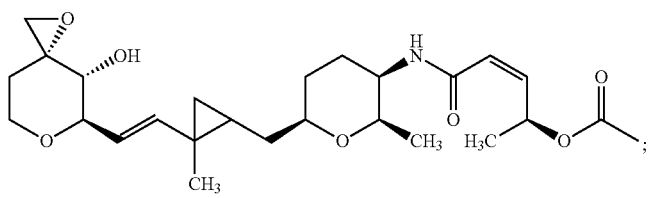

-continued
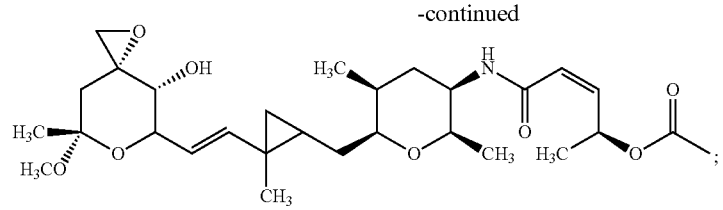
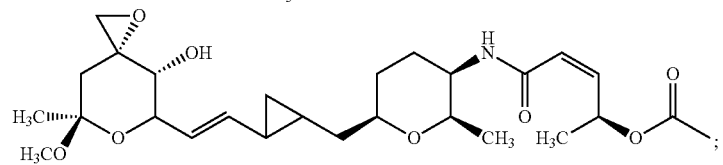
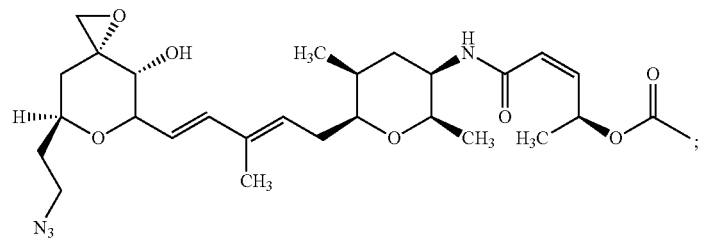
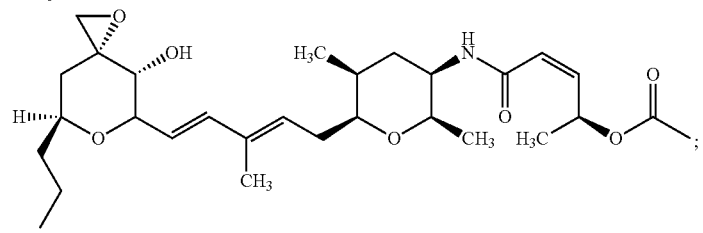
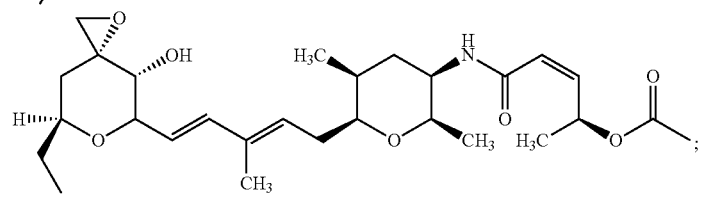
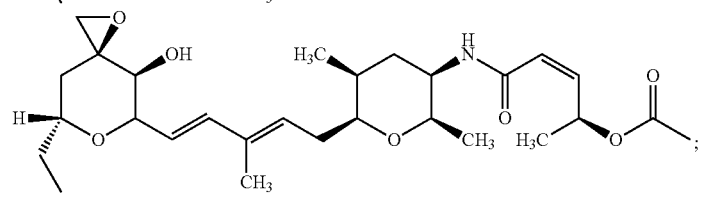
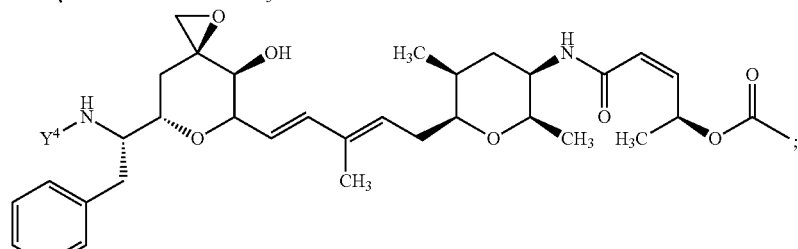
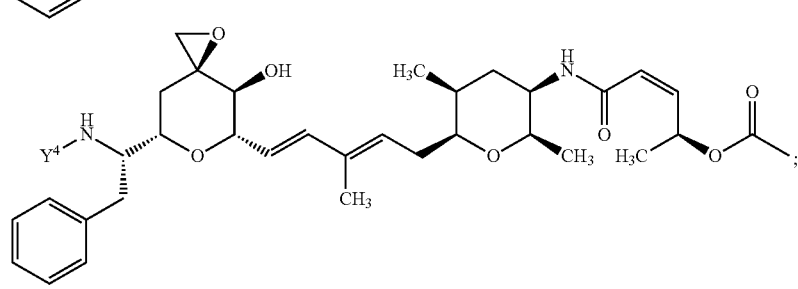

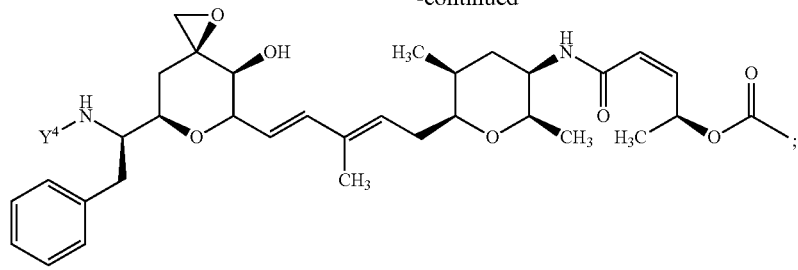
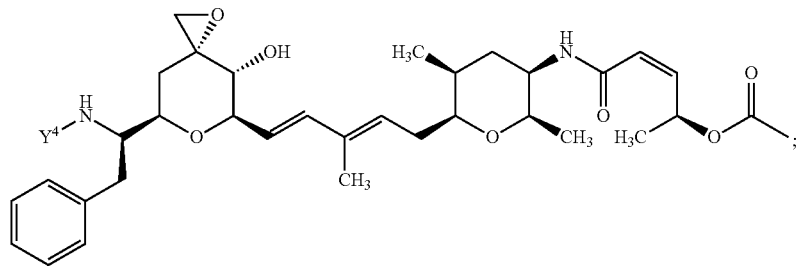
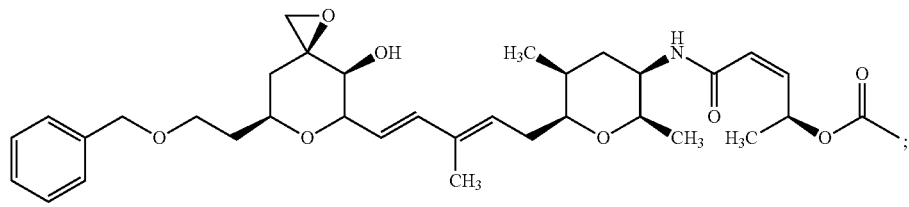
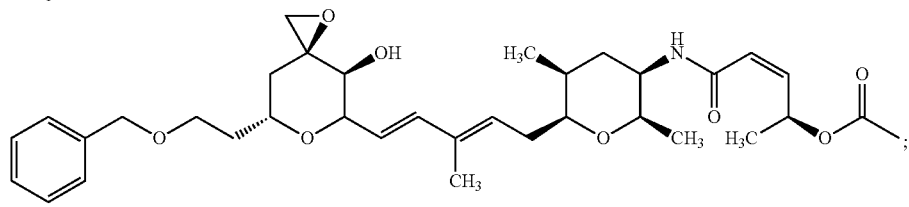
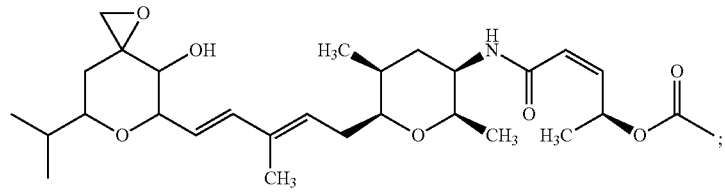
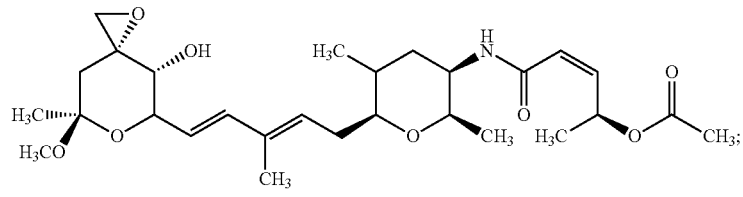
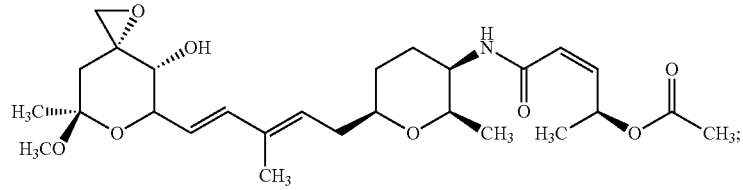
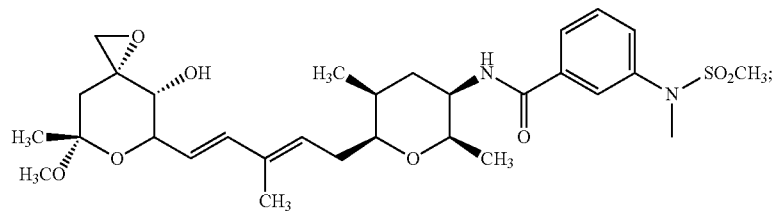

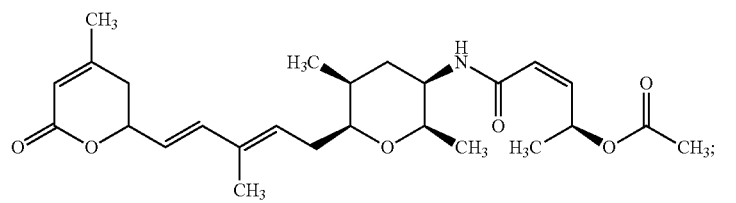
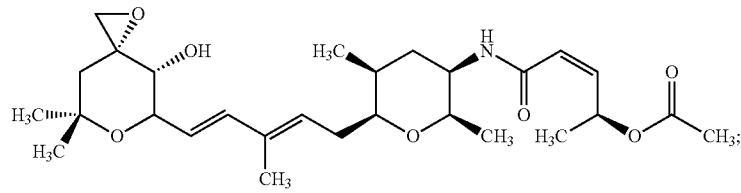
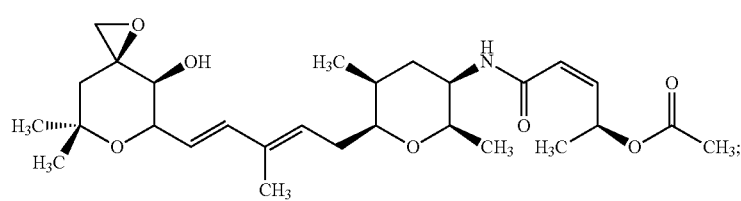
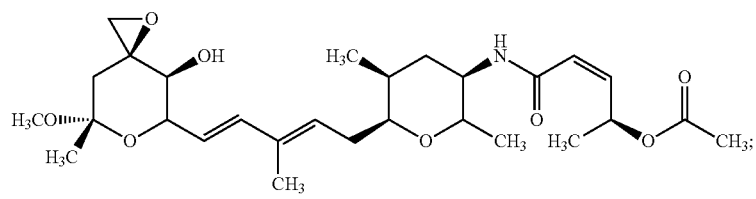
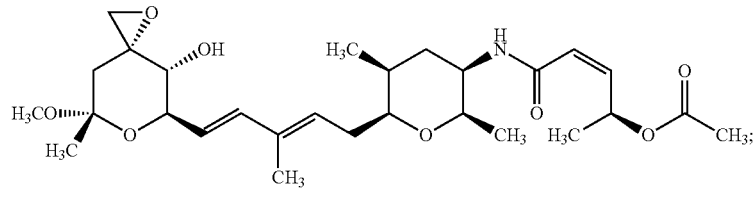
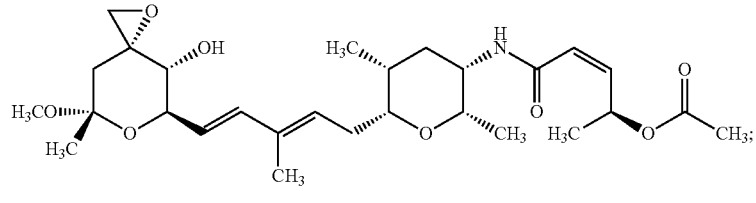
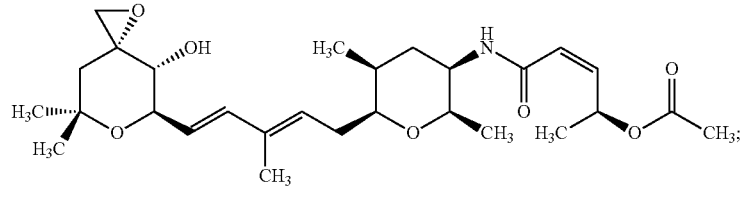
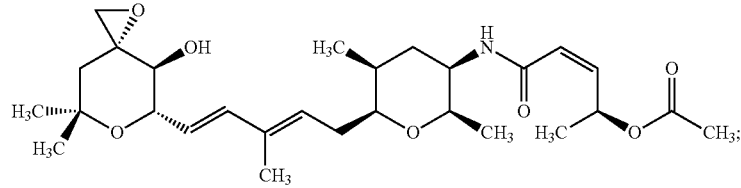

and stereoisomers, pharmaceutically acceptable salts, prodrugs (e.g., ester) or antibody conjugates thereof.

Embodiments of the disclosure also include compounds of the Formula V and stereoisomers, pharmaceutically acceptable salts, prodrugs (e.g., ester) or antibody conjugates (see, e.g., U.S. Pat. No. 8,663,643, which is incorporated by reference as if fully set forth herein) thereof:

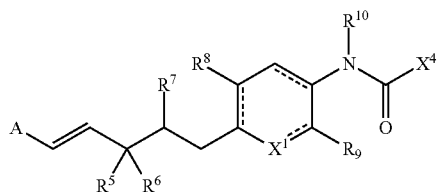

V wherein $X^1$, A, $R^5$-R-$R^{10}$ are defined herein for compounds of the Formulae I and Ia-Ic are defined herein; and $X^4$ is aryl or a 5- to 6-membered heterocyclic ring.

An example of compounds encompassed by the Formula V include compounds of the Formula Va:

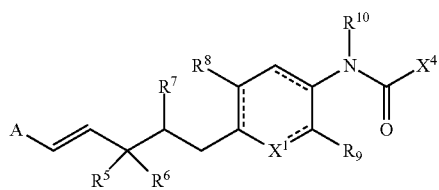

wherein $X^4$ is:

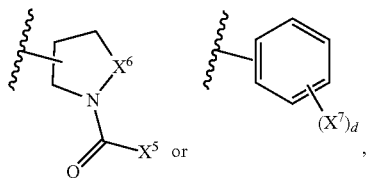

wherein $X^6$ is $CH_2$ or $-CH_2CH_2-$; $X^5$ is alkoxy, or NHalkyl; and $X^7$ is $C(O)OR^{21}$, $C(O)NR^{21}R^{22}$, $OR^{21}$ or $NR^{21}R^{22}$, wherein $R^{21}$ is H, alkyl or acyl; and $R^{22}$ is H or $S(O)_qR^{23}$, wherein $R^{23}$ is alkyl or aryl; q is 0, 1 or 2; and d is 1 or 2.

Examples of $X^4$ groups include:

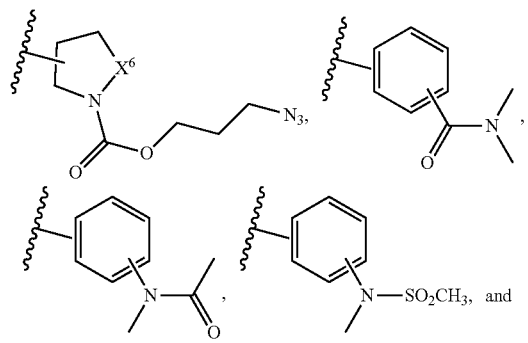

-continued

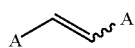

Examples of compounds of the formula Va include compounds of the Formula (Vb) and stereoisomers, pharmaceutically acceptable salts, prodrugs (e.g., ester) or antibody conjugates (see, e.g., U.S. Pat. No. 8,663,643, which is incorporated by reference as if fully set forth herein) thereof:

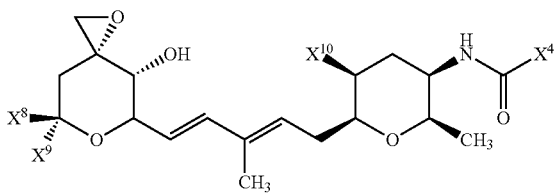

Vb $X^8$ and $X^9$ are each, independently, H, alkyl or alkoxy or, $X^8$ and $X^9$ together with the carbon atom to which they are attached, form a cycloalkyl group (e.g., cyclopropyl).

An example of a compound of the Formulae V, Va, and Vb includes the compound of the formula:

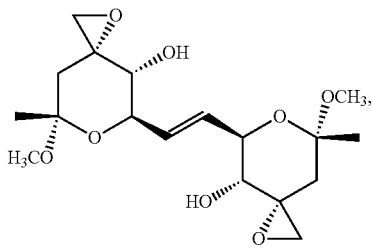

Embodiments of the disclosure also include compounds of the Formula VI and stereoisomers, pharmaceutically acceptable salts, prodrugs (e.g., ester) or antibody conjugates (see, e.g., U.S. Pat. No. 8,663,643, which is incorporated by reference as if fully set forth herein) thereof:

VI wherein A is defined herein and each A can be the same or different.

Examples of compounds of the Formula VI include:

33
-continued

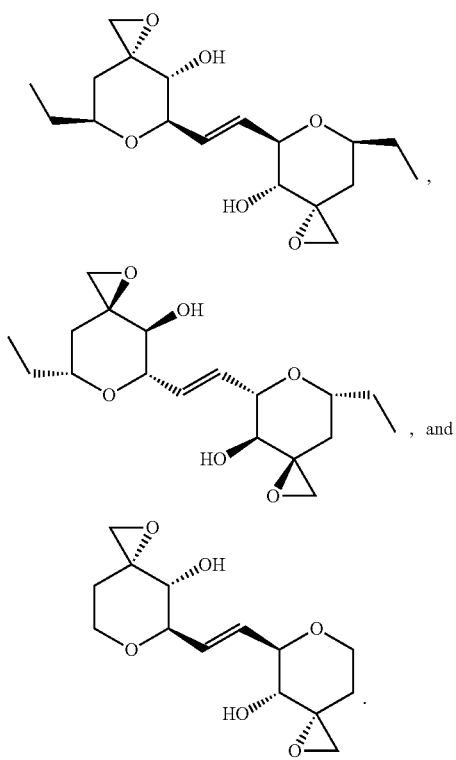

Still other embodiments are directed to a process for preparing compounds having Formulae I and Ia-Ic and stereoisomers, pharmaceutically acceptable salts, prodrugs (e.g., ester) or antibody conjugates thereof, the method comprising:

contacting a compound of the Formula II:

II wherein:
A is selected from the group consisting of groups $A^1$-$A^5$:

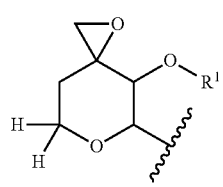

A$^1$

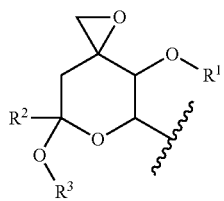

A$^2$

34
-continued

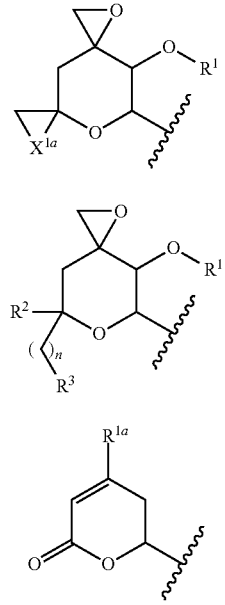

A$^3$

A$^4$

A$^5$ n is an integer from 1 to 10 (e.g., from 1 to 5; from 1 to 3; or from 2 to 5);

$X^{1a}$ is —(CH$_2$)$_g$—$X^{1b}$—, wherein g is an integer from 1 to 5 and $X^{1b}$ is a bond, O or NR$^{1a}$, wherein R$^{1a}$ is H or alkyl;

R$^1$ is selected from the group consisting of H, a hydroxyl protecting group, and alkyl;

R$^2$ and R$^3$ are each independently selected from the group consisting of H and alkyl;

R$^4$ is selected from the group consisting of —N$_3$, alkyl, aryl, heteroaryl, alkyl-X$^2$, and arylalkyl-X$^2$—, wherein X$^2$ is —O— or NH, or R$^4$ is —C(O)R″, wherein R$^{14}$ is selected from the group consisting of H, —OH, alkyl-O—, and —N(R$^{15}$)$_2$, wherein each R$^{15}$ is independently selected from the group consisting of H and alkyl;

with a compound of the Formula III:

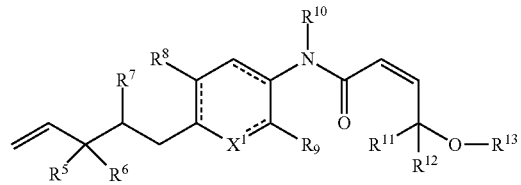

III wherein:
R$^5$ and R$^8$-R$^{12}$ are each independently selected from the group consisting of H and alkyl;

R$^6$ and R$^7$, together, form a double bond or a cycloalkyl group; and

R$^{13}$ is selected from the group consisting of H, alkyl, and —C(O)R$^{16}$, wherein R$^{16}$ is selected from the group consisting of H, —OH, alkyl, alkyl-O—, and —NR$^{17}$R$^{18}$, wherein R$^{17}$ and R$^{18}$ are each independently selected from the group consisting of H and alkyl or R$^{17}$ and R$^{18}$ together with the nitrogen atom to which they are bound, form a 5- to 6-membered heterocyclic ring;

in the presence of an olefin metathesis catalyst;
to form compounds having Formulae I, and Ia-Ic and stereoisomers, pharmaceutically acceptable salts, prodrugs (e.g., ester) or antibody conjugates thereof.

In some embodiments, the compound of the Formula II is a compound of the formula IIa:

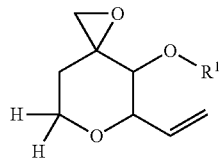

IIa wherein $R^1$ is defined herein; and stereoisomers thereof. In some embodiments, compounds of the formula IIa include the compound of the formula:

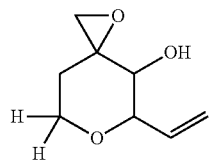

and, specifically, a compound of the formula:

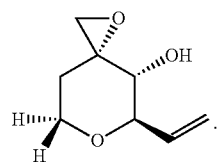

In some embodiments, the compound of the Formula II is a compound of the formula IIb:

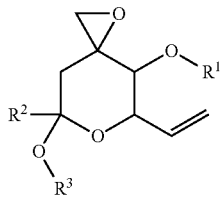

IIb wherein $R^1$-$R^3$ are defined herein and stereoisomers thereof. In some embodiments, compounds of the formula IIb include the compounds of the formulae:

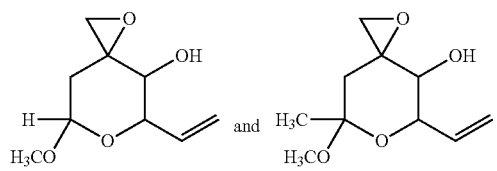

and, specifically, compounds of the formulae:

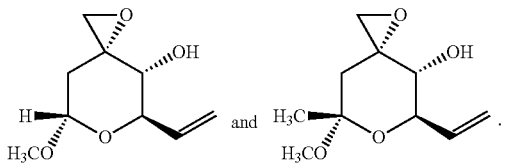

In some embodiments, the compound of the Formula II is a compound of the formula IIc:

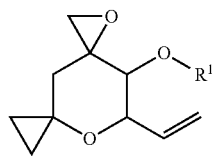

IIc wherein $R^1$ is defined herein; and stereoisomers thereof. In some embodiments, compounds of the formula IIc include the compound of the formula:

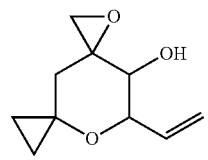

and, specifically, a compound of the formula:

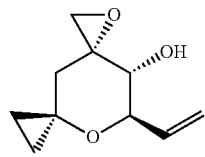

In some embodiments, the compound of the Formula II is a compound of the formula IId:

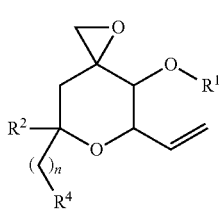

IId wherein n, $R^1$, $R^2$, and $R^4$ are defined herein; and stereoisomers thereof. In some embodiments, compounds of the formula IId include the compound of the formula:

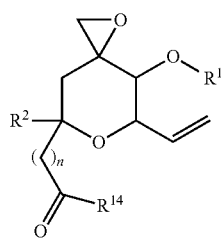

wherein n, R$^1$, R$^2$, $^{and}$ R$^{14}$ are defined herein; and, specifically, a compound of the formula:

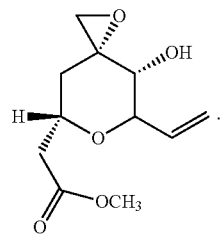 [SMILES: C=CC1O[C@H](CC(=O)OC)C[C@@]2(CO2)[C@@H]1O]

In some embodiments, the compound of the Formula III is a compound of the Formula IIIa:

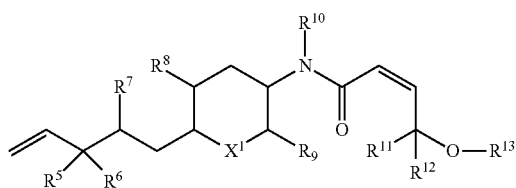

wherein X$^1$ and R$^5$-R$^{13}$ are defined herein. In some embodiments, the compound of the Formula III is a compound of the Formula IIIb:

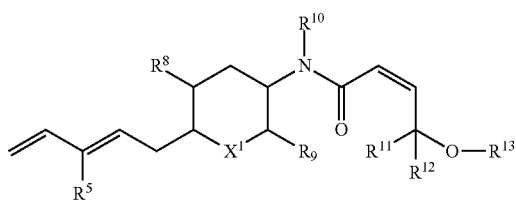

wherein X$^1$, R$^5$, and R$^8$-R$^{13}$ are defined herein. In still other embodiments, the compound of the Formula III is a compound of the Formula IIIc:

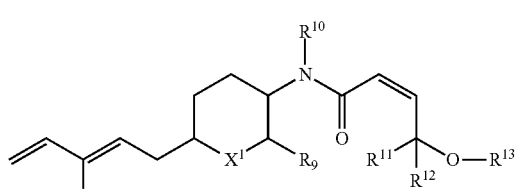

wherein X$^1$, R$^5$, and R$^9$-R$^{13}$ are defined herein. In yet other embodiments, the compound of the Formula III is a compound of the Formula IIId:

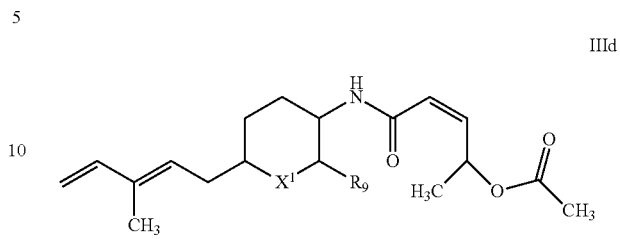

wherein X$^1$ and R$^9$ are defined herein. In some embodiments, in the compounds of the Formula III, IIIa, IIIb, IIIc or IIId, X$^1$ is O.

In some embodiments, the compound of the Formula III is a compound of the Formula IV:

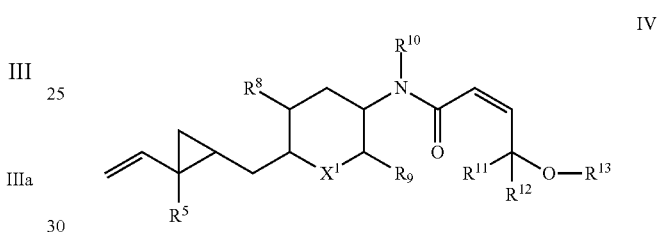

wherein X$^1$, R$^5$, and R$^8$-R$^{13}$ are defined herein. In some embodiments, the compound of the Formula IV is a compound of the Formula IVa:

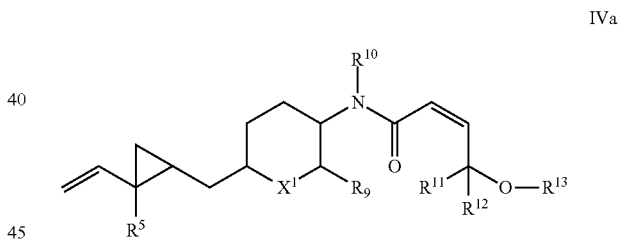

wherein X$^1$, R$^5$, and R$^9$-R$^{13}$ are defined herein. In yet other embodiments, the compound of the Formula IV is a compound of the Formula IVb:

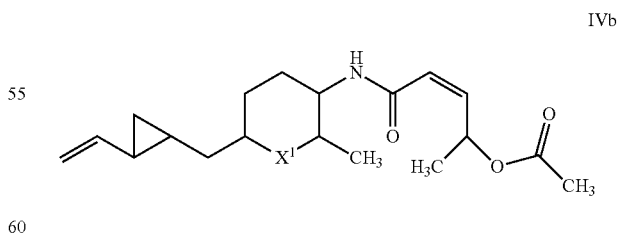

wherein X$^1$ is defined herein. In some embodiments, in the compounds of the Formula IV, IVa, and IVb, X$^1$ is O.

Those of ordinary skill in the art will recognize that compounds described herein contain chiral centers. All diastereomers of the compounds described herein are contemplated herein, as well as racemates. Those of ordinary skill in the art will also recognize that compounds described herein comprise at double bonds each of which can have the E (engegen) or the Z (zusammen) configuration. All isomers of the compounds described herein (e.g., E,E; Z,Z; E,Z; and Z,E) are contemplated herein.

Various embodiments also contemplate pharmaceutical compositions comprising one or more compounds of the various embodiments described herein and one or more pharmaceutically acceptable carriers, diluents, excipients or combinations thereof. A "pharmaceutical composition" refers to a chemical or biological composition suitable for administration to a subject (e.g., mammal). Such compositions may be specifically formulated for administration via one or more of a number of routes, including but not limited to buccal, cutaneous, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In addition, administration can by means of capsule, drops, foams, gel, gum, injection, liquid, patch, pill, porous pouch, powder, tablet, or other suitable means of administration.

A "pharmaceutical excipient" or a "pharmaceutically acceptable excipient" comprises a carrier, sometimes a liquid, in which an active therapeutic agent is formulated. The excipient generally does not provide any pharmacological activity to the formulation, though it may provide chemical and/or biological stability, and release characteristics. Examples of suitable formulations can be found, for example, in Remington, The Science And Practice of Pharmacy, 20th Edition, (Gennaro, A. R., Chief Editor), Philadelphia College of Pharmacy and Science, 2000, which is incorporated by reference in its entirety.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions described herein is contemplated. Supplementary active compounds can also be incorporated into the compositions.

Pharmaceutical compositions may be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Oral forms of administration are also contemplated herein. The pharmaceutical compositions may be orally administered as a capsule (hard or soft), tablet (film coated, enteric coated or uncoated), powder or granules (coated or uncoated) or liquid (solution or suspension). The formulations may be conveniently prepared by any of the methods well-known in the art. The pharmaceutical compositions may include one or more suitable production aids or excipients including fillers, binders, disintegrants, lubricants, diluents, flow agents, buffering agents, moistening agents, preservatives, colorants, sweeteners, flavors, and pharmaceutically compatible carriers.

For each of the recited embodiments, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multilayer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

The amount of active compound in a therapeutic composition according to various embodiments may vary according to factors such as the disease state, age, gender, weight, patient history, risk factors, predisposition to disease, administration route, pre-existing treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

"Dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on the unique characteristics of the active compound and the particular therapeutic effect to be achieved, and the limitations inherent in the art of compounding such an active compound for the treatment of sensitivity in individuals. In therapeutic use for treatment of conditions in mammals (e.g., humans) for which the compounds or an appropriate pharmaceutical composition thereof are effective, the compounds may be administered in an effective amount. Suitable dosages may be a composition, a pharmaceutical composition or any other compositions described herein.

For each of the recited embodiments, the dosage is typically administered once, twice, or thrice a day, although more frequent dosing intervals are possible. The dosage may be administered every day, every 2 days, every 3 days, every 4 days, every 5 days, every 6 days, and/or every 7 days (once a week). In one embodiment, the dosage may be administered daily for up to and including 30 days, preferably between 7-10 days. In another embodiment, the dosage may be administered twice a day for 10 days. If the patient requires treatment for a chronic disease or condition, the dosage may be administered for as long as signs and/or symptoms persist. The patient may require "maintenance treatment" where the patient is receiving dosages every day for months, years, or the remainder of their lives. In addition, the compositions described herein may effect prophylaxis of recurring symptoms. For example, the dosage may be administered once or twice a day to prevent the onset of symptoms in patients at risk, especially for asymptomatic patients.

The compositions described herein may be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are buccal and oral. The administration can be local, where the composition is administered directly, close to, in the locality, near, at, about, or in the vicinity of, the site(s) of disease or systemic, wherein the composition is given to the patient and passes through the body widely, thereby reaching the site(s) of disease. Local administration can be administration to the cell, tissue, organ, and/or organ system, which encompasses and/or is affected by the disease, and/or where the disease signs and/or symptoms are active or are likely to occcur. Administration can be topical with a local effect, composition is applied directly where its action is desired. Administration can be enteral wherein the desired effect is systemic (nonlocal), composition is given via the digestive tract. Administration can be parenteral, where the desired effect is systemic, composition is given by other routes than the digestive tract.

In some embodiments, various embodiments contemplate compositions comprising a therapeutically effective amount of one or more compounds of the various embodiments described herein. In some embodiments, the compositions are useful in a method for treating cancer, the method comprising administering a therapeutically effective amount of one or more compounds of the various embodiments to a patient in need thereof. In some aspects, various embodiments contemplate a compound of, e.g., the Formula I, for use as a medicament for treating a patient in need of relief from cancer. In some embodiments, the cancer includes, but is not limited to, solid tumor cell cancers including, but not limited to, pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma. Examples of hematologic malignancy include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkins disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes, such as breast, lung, cervical, prostate, ovarian, pancreatic, and renal cell cancer.

The term "therapeutically effective amount" as used herein, refers to that amount of one or more compounds of the various embodiments described herein that elicits a biological or medicinal response in a tissue system, animal or human, that is being sought by a researcher, veterinarian, medical doctor or other clinician, which includes alleviation of the symptoms of the disease or disorder being treated. In some embodiments, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the condition being treated and the severity of the condition; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician. It is also appreciated that the therapeutically effective amount can be selected with reference to any toxicity, or other undesirable side effect, that might occur during administration of one or more of the compounds described herein.

In some embodiments, therapeutically effective amounts of the compounds of the various embodiments described herein can range from approximately 0.05 to 50 mg per kilogram body weight of the recipient per day; such as about 0.1-25 mg/kg/day, or from about 0.5 to 10 mg/kg/day. Thus, for administration to a 70 kg person, for instance, the dosage range can be about 35-70 mg per day.

In some embodiments, the compounds of the various embodiments described herein have an in vitro $IC_{50}$ value against cancer cell lines (e.g., ATK 293 cell line and MDR cell line) of about below 1 nM to about 100 nM.

In some embodiments, one or more of the compounds of the various embodiments described herein can be administered in combination with at least one other anticancer agent including, but not limited to docetaxel, paclitaxel, bevacizumab (Avastin™).

Various modifications and many further embodiments thereof, in addition to those shown and described herein, will become apparent to those skilled in the art from the full contents of this document, including references to the scientific and patent literature cited herein. The subject matter herein contains important information, exemplification and guidance that can be adapted in its various embodiments and equivalents thereof.

The terms and expressions which have been employed are used as terms of description and not of limitation, and there is no intention that in the use of such terms and expressions of excluding any equivalents of the features shown and described or portions thereof, but it is recognized that various modifications are possible. Thus, it should be understood that although various embodiments have been specifically disclosed herein, modification and variation of the concepts herein disclosed may be resorted to by those of ordinary skill in the art, and that such modifications and variations are considered to be within the scope of the various embodiments defined by the appended claims.

The term "alkyl" as used herein refers to substituted or unsubstituted straight chain and branched alkyl groups and cycloalkyl groups having from 1 to 40 carbon atoms ($C_1$-$C_{40}$, 1 to about 20 carbon atoms ($C_1$-$C_{20}$), 1 to 12 carbons ($C_1$-$C_{12}$), 1 to 8 carbon atoms ($C_1$-$C_8$), or, in some embodiments, from 1 to 6 carbon atoms ($C_1$-$C_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Representative substituted alkyl groups can be substituted one or more times with any of the groups listed herein, for example, amino, hydroxy, cyano, carboxy, nitro, thio, alkoxy, and halogen groups. The term "alkyl" also encompasses substituted or unsubstituted straight chain and branched divalent alkyl groups, such as —$CH_2$—, —$CH_2CH_2$—, —$CH_2CH_2CH_2$—, and —$CH_2CH$($CH_3$)$CH_2$—.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. In some embodiments, cycloalkyl groups can have 3 to 6 carbon atoms ($C_3$-$C_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups.

The term "heterocyclyl" and "heterocyclic" as used herein refers to substituted or unsubstituted aromatic and non-aromatic ring compounds containing 3 or more ring members, of which, one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$). A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. Representative heterocyclyl groups include, but are not limited to piperidynyl, piperazinyl, morpholinyl, furanyl, pyrrolidinyl, pyridinyl, pyrazinyl, pyrimidinyl, triazinyl, thiophenyl, tetrahydrofuranyl, pyrrolyl, oxazolyl, imidazolyl, triazyolyl, tetrazolyl, benzoxazolinyl, and benzimidazolinyl groups.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to alkylamines, arylamines, arylalkylamines; dialkylamines, diarylamines, diaralkylamines, heterocyclylamines and the like; and ammonium ions.

The terms "halo," "halogen," or "halide" group, as used herein, by themselves or as part of another substituent, mean, unless otherwise stated, a fluorine, chlorine, bromine, or iodine atom.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, including the compounds disclosed and described herein. Examples of prodrugs include, but are not limited to, derivatives and metabolites of a compound described herein that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

The term "hydroxyl protecting group" refers to groups that prevent reaction at a hydroxyl group. Examples of suitable oxygen protecting groups include, but nare not limited to silyl protecting groups (e.g., trimethylsilyl, t-butyldimethylsilyl, and t-butyl diphenylsilyl), tetrahydropyranyl protecting groups, ethoxyethyl protecting groups, benzyl protecting groups, naphthylmethyl protecting groups, p-methoxybenzyl ethers, and the like. See Peter G. M Wuts and Theodora W. Greene, Greene's Protective Groups in Organic Synthesis ($4^{th}$ ed. 2007) for other commonly-used protecting groups for hydroxyl groups.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference.

In the methods described herein, the steps can be carried out in any order without departing from the principles described herein, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substituted" as used herein refers to a group (e.g., alkyl, aryl, and heteroaryl) or molecule in which one or more hydrogen atoms contained thereon are replaced by one or more substituents. The term "substituent" as used herein refers to a group that can be or is substituted onto a molecule or onto a group. Examples of substituents include, but are not limited to, a halogen (e.g., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R, wherein R can be, for example, hydrogen, alkyl, -(alkyl-O)$_q$— (wherein q=an integer from 1 to 1000, e.g., from 1 to 500, 1 to 50, and 1 to 5), acyl, cycloalkyl, aryl, aralkyl, heterocyclyl, heteroaryl, or heteroarylalkyl, wherein each alkyl, acyl, cycloalkyl, aryl, aralkyl, heterocyclyl, heteroaryl, or heteroarylalkyl can each be substituted. A non-limiting example of an -(alkyl-O)$_q$— group includes groups of the formula —CH$_2$CH$_2$OCH$_2$CH$_2$OCH$_2$CH$_2$O— and the group of the formula —CH$_2$CH$_2$OCH$_2$CH$_2$O—.

EXAMPLES

The embodiments described herein can be better understood by reference to the following, non-limiting examples which are offered by way of illustration.

Example 1

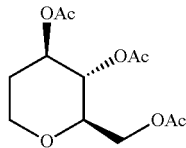 [SMILES: CC(=O)OC[C@H]1OCC[C@@H](OC(C)=O)[C@@H]1OC(C)=O]

To a solution of tri-O-acetoxy-D-glucal (5.00 g, 18.4 mmol, 1.0 equiv) in EtOAc (50 mL) was added 10% Pd/C (0.195 g, 1.84 mmol, 0.10 equiv). The reaction vessel was equipped with a rubber septum and the mixture was degassed and backfilled with H2 three times. The reaction vessel was then equipped with a balloon of H2 and allowed to stir for 12 h. The rubber septum was removed from the reaction vessel and DCM (50 mL) was added. The mixture was filtered over a pad of celite and washed with CH2Cl2. The filtrate was evaporated to give clear oil and proceed for the next step without further purification. $^1$H-NMR (400 MHz, CDCl$_3$) δ 4.96-4.91 (m, 2H), 4.21 (dd, J=12.2, 4.9 Hz, 1H), 4.08-3.99 (m, 2H), 3.52-3.46 (m, 2H), 2.00 (s, 9H), 2.00-1.99 (m, 1H), 1.83-1.76 (m, 1H); $^{13}$C-NMR (100 MHz, CDCl$_3$) δ 170.6, 170.3, 169.7, 77.2, 72.2, 69.1, 65.3, 62.6, 30.8, 20.8, 20.7, 20.6.

Example 2

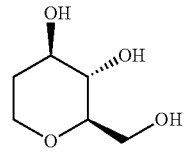

The compound of Example 1 was dissolved in MeOH (40 mL) and K$_2$CO$_3$ (0.025 g, 0.184 mmol, 0.01 equiv) was added. The reaction was judged complete after 9 hrs by checking the TLC. The MeOH was evaporated and proceed for the next step without further purification.

Example 3

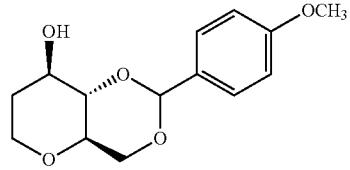

The compound of Example 2 was dissolved in DMF (40 mL). To the solution was added p-anisaldehyde dimethylacetal (3.44 mL, 3.68 g, 20.2 mmol, 1.2 equiv) and CSA (1.07 g, 4.59 mmol, 0.25 equiv). The reaction vessal was equipped with a rubber septum and stirred for 24 hrs over an atmosphere of argon. The reaction was quenched with a sat. NaHCO$_3$ solution. EtOAc (100 mL) was added and the solution was extracted. The aqueous phase was extracted again with EtOAc (100 mL). The combined organic extracts were washed with brine (2×50 mL), dried over MgSO$_4$, and evaporated under vacuum. The residue was purified by chromatography over silica gel (hexane/EtOAc=5:4) to yield a colorless oil (3.46 g, 12.88 mmol, 70%). $^1$H-NMR (400 MHz, CDCl$_3$) δ 7.41 (d, J=8.4 Hz, 2H), 6.89 (d, J=8.4 Hz, 2H), 5.52 (s, 1H), 4.26 (dd, J=10.3, 4.8 Hz, 1H), 4.01-3.98 (m, 1H), 3.88-3.84 (m, 1H), 3.80 (s, 3H), 3.69 (t, J=10.2 Hz, 1H), 3.57 (t, J=10.2 Hz, 1H), 3.44-3.40 (m, 1H), 3.39-3.33 (m, 1H), 2.5 (brs, 1H), 2.05-2.02 (m, 1H), 1.83-1.79 (m, 1H).

Example 4

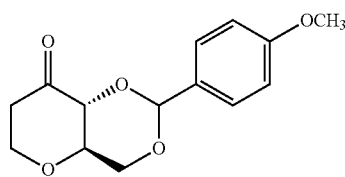

To the solution of the compound of Example 3 (1.5 g, 5.35 mmol) in DCM (25 ml) was added NaHCO$_3$ (2.69 g, 32.1 mmol, 6.0 equiv) followed by DMP (3.39 g, 8.0 mmol, 1.5 equiv). The mixture was stirred at room temperature until TLC analysis indicated consumption of the starting material (approx. 2 h). To the reaction was added 1.0 M Na$_2$S$_2$O$_3$ (30 mL) and DCM (75 mL). The biphasic mixture was stirred until both layers become clear and homogeneous (approx. 10 mins). The mixture was extracted with DCM. The combined organic extracts were washed with brine, dried over MgSO$_4$, and evaporated. Purification by chromatography on silica gel (hexanes/EtOAc=6:4). $^1$H-NMR (400 MHz, CDCl$_3$) δ 7.42 (d, J=8.4 Hz, 2H), 6.87 (d, J=8.4 Hz, 2H), 5.54 (s, 1H), 4.40 (dd, J=10.3, 4.5 Hz, 1H), 4.33-4.30 (m, 2H), 3.88-3.82 (m, 2H), 3.79 (s, 3H), 3.71-3.65 (m, 1H), 2.84-2.78 (m, 1H), 2.52 (d, J=13.6 Hz, 1H); $^{13}$C-NMR (100 MHz, CDCl$_3$) δ 199.7, 160.1, 129.0, 127.6, 113.5, 101.8, 83.5, 74.2, 69.1, 67.9, 55.2, 41.8.

Example 5

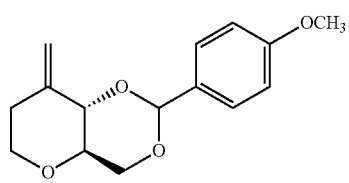

To a suspension of methyltriphenylphosphonium bromide (1.85 g, 5.18 mmol) in dry THF (15 mL) was added tBuOK (1.0 M solution in THF, 5.0 mL) at 0° C. The yellow mixture was stirred at 0° C. for 30 min. A solution of the compound of Example 5 (500 mg, 1.79 mmol) in 5 mL of THF was added to the reaction mixture. The yellow suspension was stirred at room temperature for further 4 h. After that the reaction was quenched with addition of water, and the layers were separated and extracted with 50 mL of ether, washed with brine. It was then dried with MgSO4, filtered, and the solvent was removed in vacuo. The crude residue was purified by flash column chromatography (hexanes/EtOAc=7:3) to afford the product in 82% yield. $^1$H-NMR (400 MHz, CDCl$_3$) δ 7.45 (d, J=8.4 Hz, 2H), 6.90 (d, J=8.4 Hz, 2H), 5.61 (s, 1H), 5.09 (s, 1H), 4.89 (s, 1H), 4.26 (dd, J=10.3, 4.7 Hz, 1H), 4.06-3.99 (m, 2H), 3.81 (s, 3H), 3.74 (t, J=10.2 Hz, 1H), 3.54 (t, J=10.2 Hz, 1H), 3.33-3.29 (m, 1H), 2.55-2.51 (m, 1H), 2.35 (d, J=12.6 Hz, 1H).

Example 6

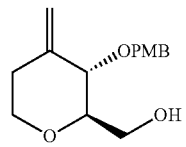

To a solution of the compound of Example 5 (384 mg, 1.39 mmol, 1.0 equiv) in toluene (13 mL) at −78° C. under an atmosphere of Argon was added DIBAL-H (4.17 mL, 4.17 mmol, 3.0 equiv) via syringe at a rate that did not allow the internal temperature exceed −60° C. The reaction was stirred at −78° C. for 1 hr. The reaction vessel was then placed into a −10° C. ice/NaCl bath and monitored closely by TLC until consumption of the starting material was observed (approximately 30 mins). MeOH was carefully added dropwise via pipette until bubbling ceased. EtOAc (25 mL) and sat. Rochelle's salt (5 mL) was added. The reaction mixture was allowed to warm to room temperature and stirred for 2 h. The EtOAc was extracted, washed with sat. NaCl, and dried over MgSO$_4$. The crude residue was purified by flash column chromatography (hexanes/EtOAc=7:3) to afford the product in 80% yield. $^1$H-NMR (400 MHz, CDCl$_3$) δ 7.29 (d, J=8.2 Hz, 2H), 6.90 (d, J=8.2 Hz, 2H), 5.12 (s, 1H), 4.92 (s, 1H), 4.65 (d, J=11.0 Hz, 1H), 4.44 (d, J=11.0 Hz, 1H), 4.04-3.95 (m, 1H), 3.85-3.75 (m, 5H), 3.70 (q, J=5.9 Hz, 1H), 3.46-3.33 (m, 1H), 3.22 (m, 1H), 2.36-2.32 (m, 2H); $^{13}$C-NMR (100 MHz, CDCl$_3$) δ 159.3, 144.3, 129.9, 129.5, 113.8, 106.6, 81.8, 72.4, 68.6, 62.6, 55.1, 35.3.

Example 7

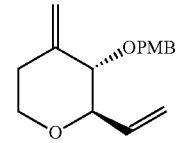

To the solution of the compound of Example 6 (155 mg, 0.58 mmol) in DCM (6 ml) at 0° C. was added NaHCO$_3$ (292 mg, 3.48 mmol, 6.0 equiv) followed by DMP (497 mg, 1.17 mmol, 2.0 equiv). The mixture was then stirred at room temperature until TLC analysis indicated consumption of the starting material (approx. 2 h). To the reaction was added 1.0 M Na$_2$S$_2$O$_3$ (5 mL) and DCM (15 mL). The biphasic mixture was stirred until both layers become clear and homogeneous (approx. 10 mins). The mixture was extracted with DCM. The combined organic extracts were washed with brine, dried over MgSO$_4$, evaporated and proceed for the next step without further purification.

To a suspension of methyltriphenylphosphonium bromide (572 mg, 1.60 mmol, 4 equiv) in dry THF (6 mL) was added tBuOK (1.0 M solution in THF, 1.2 mL) at 0° C. The yellow mixture was stirred at 0° C. for 30 min. A solution of the crude aldehyde in 2 mL of THF was added to the reaction mixture. The yellow suspension was stirred at room temperature for further 2 h. After that the reaction was quenched with addition of water, and the layers were separated and extracted with 50 mL of ether, washed with brine. It was then dried with MgSO$_4$, filtered, and the solvent was removed in vacuo. The crude residue was purified by flash column chromatography (hexanes/EtOAc=8:2) to afford the product in 81% yield. $^1$H-NMR (400 MHz, CDCl$_3$) δ 7.27 (d, J=8.4 Hz, 2H), 6.87 (d, J=8.4 Hz, 2H), 5.96 (ddd, J=16.9, 10.6, 5.9 Hz, 1H), 5.38 (d, J=17.3 Hz, 1H), 5.25 (d, J=10.6 Hz, 1H), 5.11 (s, 1H), 4.93 (s, 1H), 4.60 (d, J=11.0 Hz, 1H), 4.45 (d, J=11.0 Hz, 1H), 4.00 (m, 1H), 3.81 (s, 3H), 3.71 (t, J=7.1 Hz, 1H), 3.60 (m, 1H), 3.46 (td, J=10.6, 3.9 Hz, 1H), 2.37-2.32 (m, 1H); $^{13}$C-NMR (100 MHz, CDCl$_3$) δ 159.1, 143.9, 135.9, 130.0, 129.5, 117.4, 113.6, 107.4, 82.2, 80.5, 72.3, 67.7, 55.1, 34.9.

Example 8

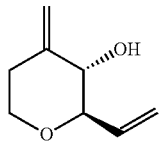

To a solution of the compound of Example 7 (62 mg, 0.24 mmol, 1.0 equiv) in DCM (2 mL) and phosphate buffer (0.2 mL, pH=7.2) at 0° C. was added DDQ (70 mg, 0.3 mmol, 1.3 equiv) in one portion. The mixture was stirred at 0° C. until TLC analysis indicated consumption of the starting material (approx. 1 h). The reaction was quenched with 50% sat. NaHCO$_3$ (2 mL) and extracted with DCM (5×2 mL). The combined organic layers were washed with sat. NaHCO$_3$, dried over MgSO4, and evaporated. The crude residue was purified by flash column chromatography (hexanes/EtOAc=7:3) to afford the product in 90% yield. $^1$H-NMR (400 MHz, CDCl$_3$) δ 5.96 (ddd, J=17.4, 10.5, 7.0 Hz, 1H), 5.39-5.33 (m, 2H), 5.11 (s, 1H), 4.92 (s, 1H), 4.04 (m, 1H), 3.82 (s, 1H), 3.56-3.29 (m, 2H), 2.50-2.23 (m, 2H), 1.81 (d, J=4.5 Hz, 1H); $^{13}$C-NMR (100 MHz, CDCl$_3$) δ 145.4, 135.9, 118.9, 106.2, 84.4, 72.4, 68.1, 35.0.

Example 9

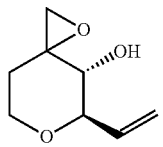

To a solution of the compound of Example 8 (70 mg, 0.5 mmol) in anhydrous DCM (5 mL) at 0° C. under argon was added NaHCO$_3$ (420 mg, 5.0 mmol) and m-CPBA (86 mg, 0.5 mmol). After stirring at 0° C. for 30 min, m-CPBA (86 mg, 0.5 mmol) was again added. After an additional 30 min, the mixture was quenched with 5% NaOH (5 mL). The aqueous phase was extracted with DCM (15×2 mL). The combined organic extracts were dried over MgSO$_4$, filtered, and concentrated. The residue was then purified via silica gel chromatography (2:1 to 1:1 hexane/ethyl acetate) to afford the product (60 mg, 88%) as amorphous solid. $^1$H-NMR (400 MHz, CDCl$_3$) δ 6.00 (ddd, J=17.3, 10.7, 5.7 Hz, 1H), 5.48-5.36 (m, 1H), 5.36-5.22 (m, 1H), 4.00 (m, 1H), 3.77-3.55 (m, 3H), 3.15 (d, J=4.5 Hz, 1H), 2.65 (d, J=4.5 Hz, 1H), 2.35 (ddd, J=14.3, 12.7, 5.6 Hz, 1H), 1.72 (d, J=10.5 Hz, 1H), 1.42 (dd, J=14.3, 1.2 Hz, 1H); $^{13}$C-NMR (100 MHz, CDCl$_3$) δ 135.5, 117.6, 81.1, 68.3, 64.7, 58.4, 49.6, 32.9.

Example 10

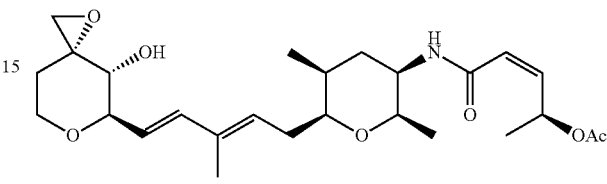

To a solution of the compound of Example 9 (5 mg, 0.032 mmol) in anhydrous dichloromethane (1 mL) at room temperature under argon was added a solution of the compound of Example 20 (11.2 mg, 0.032 mmol) in anhydrous dichloromethane (500 µL) and Grubbs' second-generation catalyst (3 mg, 0.004 mmol). The resulting mixture was heated to reflux for 5 h and then concentrated. The residue was purified via silica gel chromatography (2:1 to 1:2 hexane/ethyl acetate) to afford the product (3 mg) as amorphous solid. $^1$H-NMR of 11 (400 MHz, CDCl$_3$) δ 6.40 (d, J=15.7 Hz, 1H), 6.32-6.16 (m, 1H), 5.97 (d, J=8.9 Hz, 1H), 5.89 (dd, J=11.6, 7.9 Hz, 1H), 5.70 (d, J=11.5 Hz, 2H), 5.55-5.50 (m, 1H), 4.04-3.88 (m, 2H), 3.75 (t, J=8.5 Hz, 1H), 3.71-3.57 (m, 3H), 3.56-3.43 (m, 1H), 3.16 (d, J=4.6 Hz, 1H), 2.65 (d, J=4.5 Hz, 1H), 2.44-2.17 (m, 3H), 2.04 (s, 3H), 1.97-1.88 (m, 3H), 1.43 (s, 3H), 1.39 (d, J=6.5 Hz, 3H), 1.14 (d, J=6.4 Hz, 3H), 1.01 (d, J=7.3 Hz, 3H).

Example 11

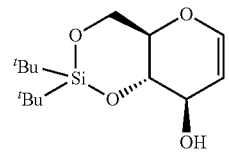 [SMILES: CC(C)(C)[Si]1(C(C)(C)C)OC[C@H]2OC=C[C@@H](O)[C@@H]2O1]

To a solution of commercially available 3,4,6-triacetyl glucal (2.0 g, 7.34 mmol) in MeOH was added K$_2$CO$_3$ (14 mg, 0.103 mmol). The resulting mixture was stirred at room temperature overnight. It was concentrated and the residue was diluted with chloroform, and the solvent was evaporated. The residue was dried to give a crude product, which was dissolved in DMF (5.7 mL) and pyridine (2.8 mL), then (tBu)$_2$Si(OTf)$_2$ (2.61 mL, 8.08 mmol) was added dropwise at −30° C. over 10 min. The resulting mixture was allowed to warm to room temperature over 1.5 h. ethyl acetate was added to the mixture and the organic phase was washed with 10% CuSO$_4$ (×2), H$_2$O (×3) and brine (×3). The combined organic layer was dried over anhydrous Na$_2$SO$_4$, concentrated to give a residue, which was purified by silica gel column chromatography (hexanes/ethyl acetate=30/1 to 18/1) to give the product (1.5 g, 71% for 2 steps) as a white solid.

Example 12

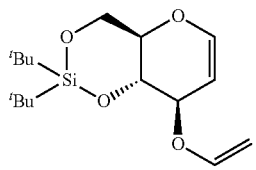 [SMILES: C=CO[C@@H]1C=CO[C@@H]2CO[Si](C(C)(C)C)(C(C)(C)C)O[C@@H]12]

To a 50 mL sealed tube was added the compound of Example 11 (1.65 g, 5.77 mmol), ethyl vinyl ether (12 mL) and Hg(OAc)$_2$ (551 mg, 1.73 mmol) sequentially. The resulting solution was heated at 65° C., and Hg(OAc)$_2$ (167 mg, 0.52 mmol) was added every 24 h for an additional 4 times. After 5 days, it was cooled to room temperature. ethyl acetate was added and washed with H$_2$O (×3) and brine (×3). The combined organic layer was dried over anhydrous Na$_2$SO$_4$, concentrated to give a residue, which was purified by silica gel column chromatography (hexanes/ethyl acetate=50/1 to 20/1) to give the product (1.17 g, 65%) and starting material (375 mg).

Example 13

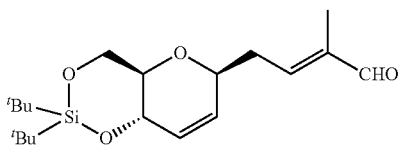 [SMILES: C/C(C=O)=C\C[C@H]1C=C[C@@H]2O[Si](C(C)(C)C)(C(C)(C)C)OC[C@H]2O1]

A solution of the compound of Example 12 (1.17 g, 3.75 mmol) in toluene was heated at 180° C. in a sealed tube for 5 h until the starting material was fully consumed as indicated by TLC. After cooling to room temperature, (α-formylethylidene)triphenylphosphorane (1.21 g, 3.81 mmol) was added and heated at reflux for an additional 4 h. The solvent was evaporated to give a residue, which was purified by silica gel column chromatography (hexanes/ethyl acetate=40/1 to 30/1) to give the product (888 mg, 67% for two steps). [α]D20 −58.6 (c 1.0, CHCl3) $^1$H-NMR (300 MHz, CDCl$_3$) δ 9.40 (s, 1H), 6.51 (t, J=6.9 Hz, 1H), 5.92 (d, J=10.2 Hz, 1H), 5.58 (d, J=10.2 Hz, 1H), 4.48-4.31 (m, 2H), 4.16 (dd, J=9.9, 4.8 Hz, 1H), 3.85 (t, J=10.2 Hz, 1H), 3.51 (ddd, J=10.2, 8.4, 5.1 Hz, 1H), 2.70-2.33 (m, 2H), 1.72 (s, 3H), 1.04 (s, 9H), 0.97 (s, 9H). $^{13}$C-NMR (100 MHz, CDCl$_3$) δ 195.0, 149.1, 141.2, 131.4, 128.4, 74.8, 74.1, 70.2, 67.2, 34.7, 27.6, 27.2, 22.8, 20.2, 9.6.

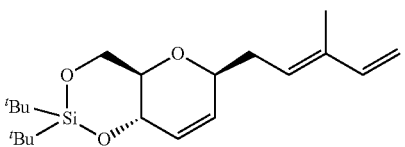 [SMILES: C=C/C(C)=C/C[C@H]1C=C[C@@H]2O[Si](C(C)(C)C)(C(C)(C)C)OC[C@H]2O1]

Example 14

To a solution of methyl triphenylphosphonium bromide (6.14 g, 17.2 mmol) in dry THF was added potassium tert-butoxide (1.92 g, 17.2 mmol) at 0° C. It was stirred at this temperature for 30 min before it was added dropwise to a solution of the aldehyde of Example 13 (2.42 g, 0.91 mmol) in THF at 0° C. The resulting solution was stirred for 2 h until the starting material was fully consumed. Water was added to quench the reaction, then it was extracted with ethyl acetate, dried over anhydrous Na$_2$SO$_4$, and concentrated to give a residue, which was purified by column chromatography (hexanes/ethyl acetate=40/1 to 25/1) to give 5 (2.05 g, 85%) as a syrup. $^1$H-NMR (300 MHz, CDCl$_3$) δ 6.38 (dd, J=17.4, 10.8 Hz, 1H), 5.86 (d, J=9.9 Hz, 1H), 5.66-5.58 (m, 1H), 5.50 (t, J=6.6 Hz, 1H), 5.11 (d, J=17.7 Hz, 1H), 4.97 (d, J=10.8 Hz, 1H), 4.44-4.35 (m, 1H), 4.26 (s, 1H), 4.18 (dd, J=9.9, 5.1 Hz, 1H), 3.87 (t, J=10.2 Hz, 1H), 3.55-3.46 (m, 1H), 2.37 (t, J=6.6 Hz, 2H), 1.73 (s, 3H), 1.05 (s, 9H), 0.98 (s, 9H).

Example 15

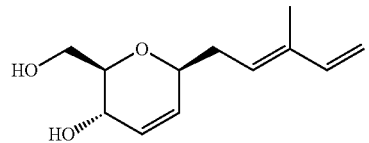

To a solution of the diene of Example 14 (2.26 g, 6.4 mmol) in dry THF (16 mL) was added TBAF (12.8 mL, 12.8 mmol) at room temperature. The resulting mixture was stirred until the starting material was fully consumed as indicated by TLC. The brown solution was concentrated to give a residue, which was purified by silica gel column chromatography (hexanes/ethyl acetate=1/1, 1% DCM) to give (1.32 g, 97%) as a colorless syrup. $^1$H-NMR (400 MHz, CDCl$_3$) δ 6.37 (dd, J=17.2, 10.8 Hz, 1H), 5.76 (dd, J=28.8, 10.4 Hz, 2H), 5.50 (t, J=7.2 Hz, 1H), 5.12 (d, J=17.2 Hz, 1H), 4.97 (d, J=10.8 Hz, 1H), 4.19 (d, J=7.2 Hz, 2H), 3.94-3.75 (m, 2H), 3.42-3.32 (m, 1H), 2.46 (br s, 2H, OH), 2.40 (d, J=6.5 Hz, 2H), 1.74 (s, 3H).

Example 16

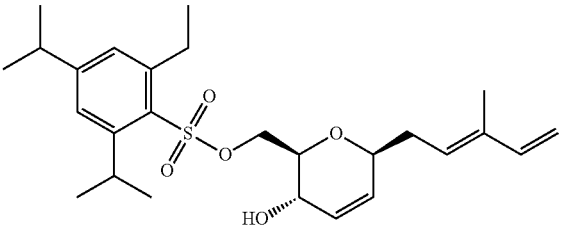 [SMILES: C=C/C(C)=C/C[C@H]1C=C[C@H](O)[C@@H](COS(=O)(=O)c2c(CC)cc(C(C)C)cc2C(C)C)O1]

To a solution of the diol of Example 15 (760 mg, 3.62 mmol) in dry DCM (5 mL) and pyridine (3 mL) was added 2,4,6-triisopropylbenzenesulfonyl chloride (1.42 g, 4.70 mmol). The resulting mixture was heated at 40° C. for 4 h. Then it was cooled to room temperature and another portion of 2,4,6-triisopropylbenzenesulfonyl chloride (200 mg, 0.66 mmol) was added and stirred overnight. Then water and DCM was added, washed by 1 N HCl, Sat NaHCO$_3$, and brine. The combined organic layer was concentrated to give a residue, which was purified by silica gel column chromatography (hexanes/ethyl acetate=5/1 to 3/1) to give a foam (1.32 g, 76%).

Example 17

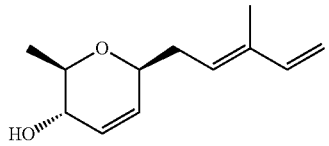

To a solution of the compound of Example 16 (1.06 g, 2.23 mmol) in freshly distilled THF (15 mL) was slowly added LAH (338 mg, 8.91 mmol) at 0° C. The resulting suspension was stirred at reflux for 1 h. Na$_2$SO$_4$.10H$_2$O was added carefully to quench the reaction. The mixture was dried over anhydrous N$_2$SO$_4$, filtered through a pad of celite and concentrated to give a residue, which was purified by silica gel column chromatography (hexanes/ethyl acetate=5/1) to give (373 mg, 86%) as colorless syrup. $^1$H-NMR (400 MHz, CDCl$_3$) δ 6.39 (dd, J=17.2, 10.8 Hz, 1H), 5.75 (q, J=11.2 Hz, 2H), 5.53 (t, J=7.2 Hz, 1H), 5.12 (d, J=17.2 Hz, 1H), 4.96 (d, J=10.8 Hz, 1H), 4.15 (t, J=7.2 Hz, 1H), 3.88 (d, J=8.0 Hz, 1H), 3.43-3.23 (m, 1H), 2.49-2.24 (m, 2H), 1.75 (s, 3H), 1.34 (d, J=6.0 Hz, 3H).

Example 18

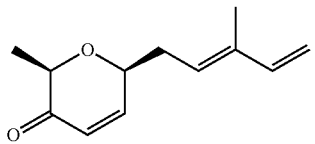

To a solution of the compound of Example 17 (360 mg, 1.86 mmol) in dry DCM (12 mL) was added Dess-Martin periodinane (1.73 g, 4.08 mmol) at 0° C. The resulting solution was gradually warmed to room temperature until the starting material was fully consumed as indicated by TLC. Then sat. NaHCO$_3$ and sat Na$_2$S$_2$O$_3$ solution was added to quenched the reaction. It was extracted with DCM, washed with brine, and dried over anhydrous Na$_2$SO$_4$. The solvent was concentrated to give a residue, which was purified by silica gel chromatography (hexanes/ethyl acetate=8/1) to give (266 mg, 74%) as a syrup and starting material (45 mg). $^1$H-NMR (400 MHz, CDCl$_3$) δ 6.91 (d, J=10.4 Hz, 1H), 6.40 (dd, J=17.2, 10.8 Hz, 1H), 6.11 (d, J=10.4 Hz, 1H), 5.55 (t, J=7.2 Hz, 1H), 5.16 (d, J=17.2 Hz, 1H), 5.01 (d, J=10.8 Hz, 1H), 4.41 (t, J=6.0 Hz, 1H), 4.09 (dd, J=12.8, 6.4 Hz, 1H), 2.61-2.50 (m, 2H), 1.78 (s, 3H), 1.40 (d, J=6.4 Hz, 3H).

Example 19

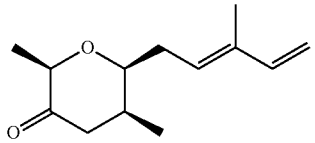

To a suspension of CuBr.Me2S (835 mg, 4.06 mmol) in freshly distilled Et2O (10 mL) was added MeLi (2.62 mL, 3.1 M, 8.31 mmol) dropwise over 10 min at −78° C. under argon. After stirring for 1 h, a solution of the compound of Example 18 (260 mg, 1.35 mmol) in Et$_2$O (4 mL) was added dropwise. Stirring was continued for an additional 2 h, and water was added carefully to quench the reaction. It was extracted with ethyl acetate, washed with brine, dried over anhydrous Na$_2$SO$_4$, and concentrated to give a residue, which was purified by silica gel column chromatography (hexanes/ethyl acetate=10/1) to give product (240 mg, 85%) as a syrup. It was immediately used for the next step. $^1$H-NMR (400 MHz, CDCl$_3$) δ 6.39 (dd, J=17.2, 10.4 Hz, 1H), 5.50 (t, J=7.2 Hz, 1H), 5.14 (d, J=17.2 Hz, 1H), 4.98 (d, J=10.8 Hz, 1H), 4.01-3.82 (m, 2H), 2.64 (dd, J=14.8, 6.0 Hz, 1H), 2.52-2.42 (m, 1H), 2.41-2.25 (m, 3H), 1.77 (s, 3H), 1.31-1.26 (m, 4H), 1.00-0.95 (m, 3H).

Example 20

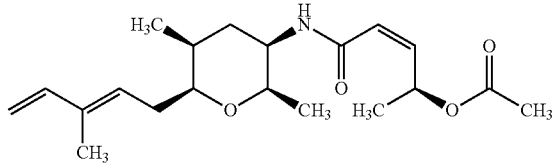 [SMILES: C=C/C(C)=C/C[C@@H]1O[C@H](C)[C@H](NC(=O)/C=C\[C@H](C)OC(C)=O)C[C@@H]1C]

To a solution of the compound of Example 19 (170 mg, 0.8 mmol) in anhydrous methanol (8 mL) at 0° C. under argon was added ammonium acetate (755 mg, 9.8 mmol) and NaBH$_3$CN (205 mg, 3.2 mmol). The reaction mixture was then gradually warmed to room temperature. After stirring for 24 h, the reaction mixture was added to aqueous NaOH (4 M, mL) to adjust the pH to a range of ~8-9 and then diluted with ethyl acetate (mL). The resulting mixture was directly dried over MgSO$_4$, filtered, and concentrated to give crude amines, which was purified by silica gel column chromatography (DCM/MeOH=15/1) to give mixture of amines.

To a solution of acid (95 mg, mmol):

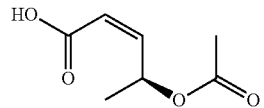

and crude amines (105 mg, 0.5 mmol) in anhydrous acetonitrile (4 mL) at room temperature under argon was added HATU (143 mg, 0.4 mmol) and DIPEA (273 μL, 1.6 mmol). The resulting mixture was stirred overnight. Sat. NH$_4$Cl was added to quench the reaction. It was extracted with ethyl acetate, dried over Na$_2$SO$_4$, concentrated to give a residue, which was purified by silica gel column chromatography (hexanes/ethyl acetate=5/1) to give pure diasteromer (60 mg). $^1$H-NMR (400 MHz, CDCl$_3$) δ 6.37 (dd, J=17.2, 10.8 Hz, 1H), 6.30-6.21 (m, 1H), 5.99 (d, J=8.4 Hz, 1H), 5.89 (dd, J=11.2, 8.0 Hz, 1H), 5.70 (d, J=11.6 Hz, 1H), 5.46 (t, J=6.4 Hz, 1H), 5.11 (d, J=17.2 Hz, 1H), 4.96 (d, J=10.4 Hz, 1H), 3.98-3.91 (m, 1H), 3.71-3.63 (m, 1H), 3.58-3.50 (m, 1H), 2.45-2.33 (m, 1H), 2.30-2.20 (m, 1H), 2.04 (s, 3H), 1.96 (s, 2H), 1.76 (s, 4H), 1.39 (d, J=6.4 Hz, 3H), 1.16 (d, J=6.4 Hz, 3H), 1.02 (d, J=7.2 Hz, 3H).

Example 21

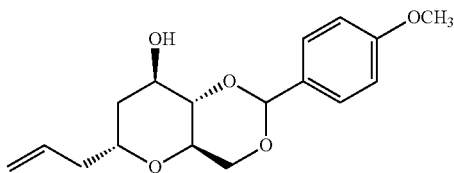

At room temperature, a catalytic amount of K₂CO₃ (58 mg, 0.42 mmol, 0.1 equiv) was added to an orange solution of known tri-acetate (1.32 g, 4.2 mmol, 1 equiv):

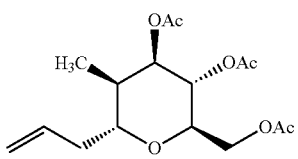 [SMILES: C=CC[C@H]1O[C@H](COC(C)=O)[C@@H](OC(C)=O)[C@H](OC(C)=O)[C@@H]1C]

dissolved in methanol (14 mL, 0.3 M) and set to stir at room temperature. After 3 h, the methanol was removed via rotary evaporation. To remove any residual methanol, the reaction flask was rinsed with chloroform and concentrated (×3) followed by high-vacuum overnight at 35° C. This provided the crude triol which was used in the subsequent step without further purification.

At room temperature, anisaldehyde dimethyl acetal (1.43 mL, 8.4 mmol, 2 equiv) and CSA (293 mg, 1.26 mmol, 0.3 equiv) were sequentially added to an orange solution of crude triol dissolved in dry DMF (8 mL, 0.5 M). If the reaction was not complete within 2 h, high vacuum was applied to help the reaction go to completion. The reaction was neutralized with triethylamine (0.5 mL, 3.53 mmol). The crude product was extracted with ethyl acetate (×3), washed with brine (×2) and dried over Na₂SO₄. Purification by flash chromatography (20% to 50% ethyl acetate/hexanes) gave 1.1 g (85% yield over 2 steps) of product as a white solid. ¹H-NMR (500 MHz, CDCl₃) δ (ppm): 7.43-7.41 (d, J=10 Hz, 2H), 6.91-6.89 (d, J=10 Hz, 2H), 5.81-5.73 (m, 1H), 5.53 (s, 1H), 5.15-5.10 (m, 2H), 4.22-4.19 (1H, J=10, 5 Hz, 1H), 4.12-4.04 (m, 2H), 3.81 (s, 3H), 3.70-3.66 (t, J=10 Hz, 1H), 3.63-3.58 (td, J=10, 5 Hz, 1H), 3.46-3.42 (t, J=10 Hz, 1H), 2.64-2.58 (m, 1H), 2.47 (br s, 1H), 2.36-2.30 (m, 1H), 2.07-2.03 (m, 1H), 1.92-1.86 (m, 1H); ¹³C-NMR (100 MHz, C CDCl₃DCl3) δ (ppm): 160.3, 134.4, 129.9, 127.7, 117.6, 113.8, 102.1, 84.7, 73.5, 69.5, 66.3, 64.2, 55.5, 36.2, 35.1; [α]D25 +20.16 (c 0.615, CHCl₃).

Example 22

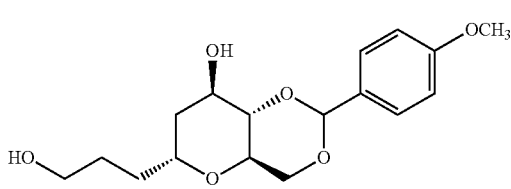

At −78° C., ozone was bubbled through a solution of the olefin of Example 21 (1.617 g, 5.28 mmol, 1 equiv) dissolved in 1/1 of MeOH/CH₂Cl₂ (26 mL, 0.2 M) until the characteristic grey-blue color developed (10 min) which was then quenched with PPh₃ (2.076 g, 7.92 mmol, 1.5 equiv). The reaction was warmed to 0° C. and stirred at this temperature for 30 min after which NaBH₄ (400 mg, 10.56 mmol, 2 equiv) was added. After stirring for 1 h at 0° C., the reaction was quenched with sat. NH₄Cl. The crude product was extracted with DCM (×3), washed with brine (×1) and dried over Na₂SO₄. Purification by flash chromatography (70% to 100% ethyl acetate/hexanes) gave 1.725 g (quantitative yield) of diol product as a white solid. ¹H-NMR (500 MHz, CDCl₃) δ (ppm): 7.42-7.40 (d, J=10 Hz, 2H), 6.91-6.89 (d, J=10 Hz, 2H), 5.51 (s, 1H), 4.30-4.25 (m, 1H), 4.20-4.17 (dd, J=10, 5 Hz, 1H), 4.05-3.99 (q, J=10 Hz, 1H), 3.80 (s, 3H), 3.74-3.72 (t, J=5 Hz, 2H), 3.69-3.65 (t, J=10 Hz, 1H), 3.63-3.58 (td, J=10, 5 Hz, 1H), 3.45-3.41 (t, J=10 Hz, 1H), 2.67 (br s, 1H), 2.23-2.15 (m, 1H), 1.97-1.94 (m, 2H), 1.87 (br s, 1H), 1.65-1.59 (m, 1H); ¹³C-NMR (100 MHz, CDCl₃) δ (ppm): 160.4, 129.9, 127.7, 113.9, 102.1, 84.6, 72.0, 69.4, 66.4, 64.3, 60.2, 55.5, 36.3, 33.5; [α]D25 +23.98 (c 0.57, CHCl₃).

Example 23

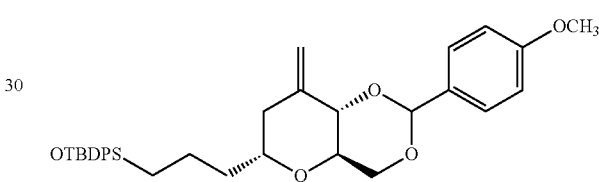

At 0° C., imidazole (750 mg, 11 mmol, 2 equiv) and TBDPS-Cl (1.3 mL, 4.96 mmol, 0.9 equiv) were sequentially added to a solution of the diol of Example 22 (1.71 g, 5.51 mmol, 1 equiv) dissolved in DCM (27 mL, 0.2 M) which was then warmed to room temperature. After stirring overnight, the reaction was diluted with water and the crude product was extracted with DCM (×3), washed with brine (×1) and dried over Na₂SO₄. Purification by flash chromatography (20% to 30% ethyl acetate/hexanes) gave 2.3235 g (77% yield) of the silyl ether as a white foam.

To a solution of silyl ether (2.3 g, 4.2 mmol, 1 equiv) dissolved in DCM (21 mL, 0.2 M) were sequentially added NaHCO₃ (2.1 g, 25.2 mmol, 6 equiv) and DMP (2.67 g, 6.29 mmol, 1.5 equiv) at 0° C. which was then warmed to room temperature. After stirring for 3 h, the reaction was quenched with a 1/1 solution of sat. Na₂S₂O₃/sat. NaHCO₃ and left to stir vigorously for 20 min. The crude product was extracted with DCM (×3), washed with brine (×1) and dried over Na₂SO₄. Purification by flash chromatography (20% to 30% ethyl acetate/hexanes) gave 1.926 g (84% yield) of ketone as a white foam.

At 0° C., KtOBu (1 M THF, 1.8 mL, 1.8 mmol, 2.5 equiv) was added to a mixture of Ph₃PCH₃Br (774 mg, 2.17 mmol, 3 equiv) in THF (5 mL). The bright yellow solution stirred at 0° C. for 20 min, then for 20 min at room temperature and cooled back down to 0° C. for the remainder of an hour. In a separate flask, ketone (390 mg, 0.713 mmol, 1 equiv) was dissolved in THF (1 mL) and added dropwise via cannula to the reaction flask at 0° C. which developed an orange color. Residual ketone was rinsed with THF (0.5 mL) and also added via cannula to the reaction flask. After stirring for 30 min at 0° C., the reaction was quenched with sat. NH₄Cl.

The crude product was extracted with ethyl acetate (×3), washed with brine (×1) and dried over Na₂SO₄.

Purification by flash chromatography (10% ethyl acetate/hexanes) gave product, 313 mg (81% yield, 52% over 3-steps) of exocyclic olefin as a clear, viscous oil. ¹H-NMR (500 MHz, CDCl₃) δ (ppm): 7.69-7.66 (m, 4H), 7.46-7.37 (m, 8H), 6.91-6.89 (d, J=10 Hz, 2H), 5.59 (s, 1H), 5.13 (s, 1H), 4.85 (s, 1H), 4.34-4.29 (q, J=10 Hz, 1H), 4.09-4.06 (dd, J=10, 5 Hz, 1H), 3.98-3.96 (d, J=10 Hz, 1H), 3.82 (s, 3H), 3.76-3.64 (m, 3H), 3.45-3.40 (td, J=10, 5 Hz, 1H), 2.74-2.70 (dd, J=15, 5 Hz, 1H), 2.26-2.23 (d, J=15 Hz, 1H), 2.09-2.02 (m, 1H), 1.76-1.69 (m, 1H), 1.06 (s, 9H); ¹³C-NMR (100 MHz, CDCl₃) δ (ppm): 160.1, 139.8, 135.7, 133.8, 133.7, 130.4, 129.8, 127.8, 127.6, 117.0, 113.7, 107.5, 101.6, 80.7, 71.6, 70.0, 67.5, 60.5, 55.4, 38.1, 33.0, 27.0, 19.3; [α]D25 +43.0 (c 0.20, CHCl₃).

Example 24

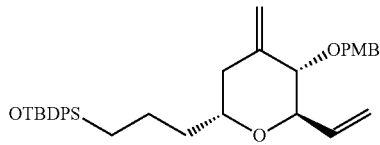

DIBAL-H (1 M in hexanes, 5.6 mL, 5.6 mmol, 3.1 equiv) was added slowly to a solution of the acetal of Example 23 (986 mg, 1.81 mmol, 1 equiv) dissolved in toluene (18 mL, 0.1 M) at −78° C. The dry ice/acetone bath was replaced with an ice/water bath to warm the reaction to 0° C. After 30 min, the reaction was quenched with ethyl acetate followed by saturated sodium potassium tartrate and then warmed to room temperature. After stirring vigorously overnight, the crude product was extracted with ethyl acetate (×3), washed with brine (×1) and dried over Na₂SO₄. Purification by flash chromatography (10% ethyl acetate/hexanes) gave 599 mg (77% yield) of primary alcohol as a clear oil.

NaHCO₃ (343 mg, 4.08 mmol, 6 equiv) and DMP (577 mg, 1.36 mmol, 2 equiv) were sequentially added at 0° C. to a solution of primary alcohol (372 mg, 0.68 mmol, 1 equiv) dissolved in DCM (7 mL, 0.1 M). The reaction warmed to room temperature and quenched after 1 h with a 1/1 solution of sat. Na₂S₂O₃/sat. NaHCO₃ and left to stir vigorously for 20 min. The crude product was extracted with DCM (×3), washed with sat. NaHCO₃ (×1) and brine (×1) and dried over Na₂SO₄. The crude product was used for the subsequent step without further purification.

At 0° C., KtOBu (1M in THF, 2.7 mL, 2.7 mmol, 4 equiv) was added to a mixture of Ph₃PCH₃Br (1.21 g, 3.4 mmol, 5 equiv) in THF (6 mL). The bright yellow solution stirred at 0° C. for 20 min, then for 20 min at room temperature and cooled back down to 0° C. for the remainder of an hour. In a separate flask, crude aldehyde (0.68 mmol, 1 equiv) was dissolved in THF (1 mL) and added dropwise via cannula to the reaction flask at 0° C. which developed a dark orange color. Residual aldehyde was rinsed with THF (0.5 mL) and also added via cannula to the reaction flask. After stirring for 10 min at 0° C., the reaction was quenched with sat. NH₄Cl. The crude product was extracted with ethyl acetate (×3), washed with brine (×1) and dried over Na₂SO₄. Purification by flash chromatography (5% to 10% ethyl acetate/hexanes) gave 251 mg (68% over 2-steps) of diene as a clear oil.

Example 25

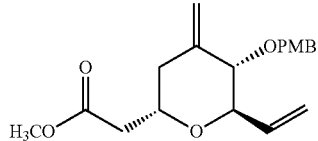

At 0° C., TBAF (1 M in THF, 0.9 mL, 0.903 mmol, 2 equiv) was added to a solution of silyl ether of Example 24 (245 mg, 0.451 mmol, 1 equiv) dissolved in THF (4.5 mL, 0.1 M) which was then warmed to room temperature. After 1.5 h, the reaction was concentrated and directly purified by flash chromatography (20% to 70% ethyl acetate/hexanes) giving 105 mg (77% yield) of primary alcohol as a clear oil.

At 0° C., NaHCO₃ (167 mg, 2.0 mmol, 6 equiv) and DMP (282 mg, 0.664 mmol, 2 equiv) were sequentially added to a solution of primary alcohol (101 mg, 0.332 mmol, 1 equiv) in DCM (3 mL, 0.1 M) which was then warmed to room temperature. After 2 h, the reaction was quenched with a 1/1 solution of sat. Na₂S₂O₃/sat. NaHCO₃ and left to stir vigorously for 20 min. The crude product was extracted with DCM (×3), washed with sat. NaHCO₃ (×1) and brine (×1) and dried over Na₂SO₄. The crude product was used for the subsequent step without further purification.

Methanol (80 µL, 2.0 mmol, 6 equiv) and PDC (749 mg, 2.0 mmol, 6 equiv) were sequentially added at room temperature to a solution of crude aldehyde (0.332 mmol) in dry DMF. After stirring overnight, the black solution was diluted with ethyl acetate and water, filtered over celite and rinsing with ethyl acetate. The filtrate was concentrated and the crude product was extracted with ethyl acetate (×3), washed with brine (×1) and dried over Na₂SO₄. Purification by flash chromatography (10% to 20% ethyl acetate/hexanes) gave the desired methyl ester as a clear oil. ¹³C-NMR (100 MHz, CDCl₃) δ (ppm): 171.6, 159.3, 140.3, 134.4, 130.3, 129.6, 118.6, 114.1, 113.9, 78.9, 78.3, 69.6, 68.6, 55.4, 51.8, 40.1, 36.6.

Example 26

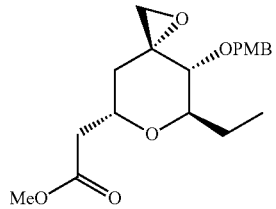

The methyl ester of Example 25 (64 mg, 0.193 mmol, 1 equiv) was dissolved in DCM (2 mL, 0.1 M) and cooled to 0° C. after which NaHCO₃ (32 mg, 0.386 mmol, 2 equiv), two pipet drops of methanol and DDQ (44 mg, 0.193 mmol, 1 equiv) were sequentially added. The dark green solution stirred at 0° C. for 1 h before a second portion of NaHCO₃, methanol and DDQ were added and stirred for another hour. The third and last portion of NaHCO₃, methanol and DDQ were added and after 1 h (still stirring at 0° C.), the reaction was quenched with sat. NaHCO₃ and diluted with DCM. The crude product was extracted with DCM (×3), washed with brine (×1) and dried over Na₂SO₄. Purification by flash chromatography (20% to 60% ethyl acetate/hexanes) gave 40.2 mg (98% yield) of alcohol as a clear oil.

VO(acac)$_2$ (9.5 mg, 0.036 mmol, 0.2 equiv) was added to alcohol methyl ester (38 mg, 0.179 mmol, 1 equiv) dissolved in DCM (2 mL, 0.1 M). The reaction was cooled to 0° C. after which TBHP (5-6 M in decane, 75 μL, 0.376 mmol, 2.1 equiv) was added and the resulting dark red solution was warmed to room temperature. After 5 h, the reaction did not progress past 1/1 starting material/product so was concentrated and purified by flash chromatography (40% to 50% ethyl acetate/hexanes) to give the desired epoxide.

Example 27

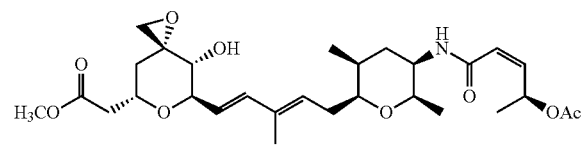 [SMILES: COC(=O)C[C@@H]1C[C@@]2(CO2)[C@H](O)[C@@H](/C=C/C(C)=C/C[C@@H]2O[C@H](C)[C@H](NC(=O)/C=C\[C@H](C)OC(C)=O)C[C@@H]2C)O1]

In three separate flasks were added the diene of Example 20 (8 mg, 0.023 mmol, 1 equiv) dissolved in DCM (0.5 mL), the epoxide of Example 26 (5.23 mg, 0.023 mmol, 1 equiv) dissolved in DCM (1 mL) and Grubbs II catalyst (3.9 mg, 0.0046 mmol, 0.2 equiv) dissolved in DCM (1 mL). Approximately ⅓ solution of the epoxide and Grubbs II were sequentially added to the diene flask and set to reflux. After 1.5 h, a second portion of epoxide and Grubbs II were added. After an additional 1.5 h, the last portion of epoxide and Grubbs II were added, rinsing the flasks with a small amount of DCM. After 2 h, the reaction was cooled to room temperature, concentrated via rotary evaporator and directly purified by flash chromatography (30% to 80% ethyl acetate/hexanes) giving 5.9 mg (47% yield) of the desired methyl ester as a clear oil. $^1$H-NMR (500 MHz, CDCl$_3$) δ (ppm): 6.37 (d, J=15.5 Hz, 1H), 6.28-6.23 (m, 1H), 6.00 (d, J=9.0 Hz, 1H), 5.89 (dd, J=11.5, 8.0 Hz, 1H), 5.70 (dd, J=11.5, 1.5 Hz, 1H), 5.62 (dd, J=15.5, 6.0 Hz, 1H), 5.51 (t, J=7.0 Hz, 1H), 4.52-4.47 (m, 1H), 4.20 (t, J=7.0 Hz, 1H), 3.95-3.93 (m, 1H), 3.69 (s, 3H), 3.66 (dd, J=6.5, 2.5 Hz, 1H), 3.54-3.51 (m, 2H), 2.99 (d, J=4.5 Hz, 1H), 2.93 (dd, J=15.5, 8.0 Hz, 1H), 2.69 (dd, J=15.5, 6.5 Hz, 1H), 2.64 (d, J=4.5 Hz, 1H), 2.41-2.36 (m, 1H), 2.27-2.21 (m, 1H), 2.16 (dd, J=14.0, 5.5 Hz, 1H), 2.04 (s, 3H), 1.96-1.93 (m, 2H), 1.82 (d, J=8.5 Hz, 1H), 1.79-1.73 (m, 1H), 1.76 (s, 3H), 1.39 (d, J=6.5 Hz, 3H), 1.15 (d, J=6.5 Hz, 3H), 1.01 (d, J=7.5 Hz, 3H); $^{13}$C-NMR (125 MHz, CDCl$_3$) δ (ppm): 171.6, 170.6, 165.0, 143.8, 138.6, 134.7, 129.6, 123.1, 122.6, 80.9, 76.1, 75.8, 69.8, 69.1, 68.9, 57.3, 52.0, 49.8, 47.2, 38.1, 36.0, 34.6, 32.1, 29.0, 21.4, 20.1, 18.0, 15.2, 12.8.

The following embodiments are provided, the numbering of which is not to be construed as designating levels of importance:

Embodiment 1 relates to a compound of the Formula I, or a stereoisomer, pharmaceutically acceptable salt, prodrug (e.g., ester) or antibody conjugate thereof:

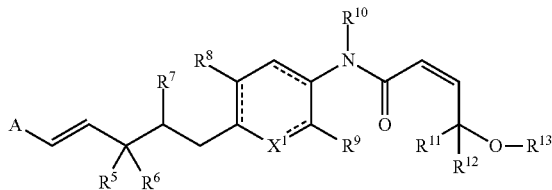

wherein
the dashed lines in the ring comprising $X^1$ are double or single bonds;
$X^1$ is selected from the group consisting of CH and N if $X^1$ is doubly bonded to an adjacent carbon atom; or
$X^1$ is selected from the group consisting of O, CH$_2$, and NH if $X^1$ is singly bonded to an adjacent carbon atom;
A is selected from the group consisting of groups $A^1$-$A^5$:

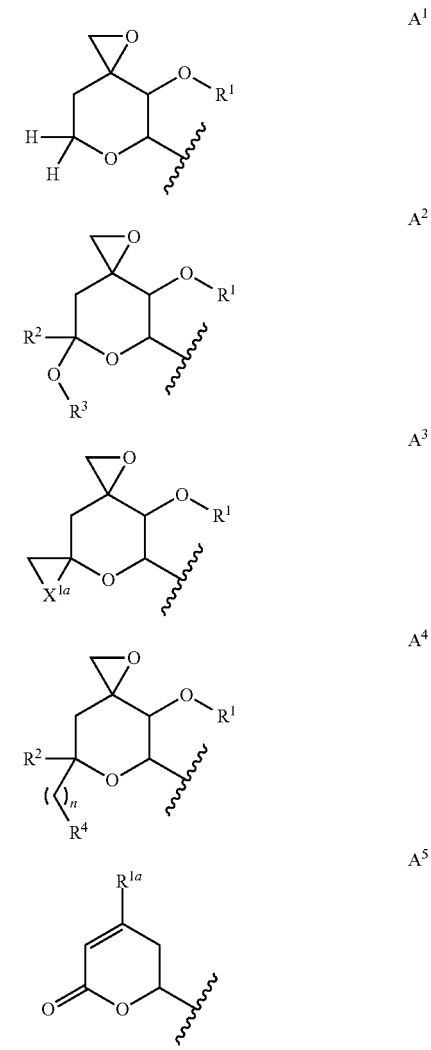

n is an integer from 1 to 10 (e.g., from 1 to 5; from 1 to 3; or from 2 to 5);
$X^{1a}$ is —(CH$_2$)$_g$—$X^{1b}$—, wherein g is an integer from 1 to 5 and kb is a bond, O or NR$^{1a}$, wherein R$^{1a}$ is H or alkyl;

R$^1$ is selected from the group consisting of H, a hydroxyl protecting group, and alkyl;

R$^2$, R$^3$, R$^5$, and R$^8$-R$^{12}$ are each independently selected from the group consisting of H and alkyl;

R$^4$ is selected from the group consisting of —N$_3$, alkyl, aryl, heteroaryl, alkyl-X$^2$—, and arylalkyl-X$^2$—, wherein X$^2$ is —O— or NH, or R$^4$ is —C(O)R$^{14}$, wherein R$^{14}$ is selected from the group consisting of H, —OH, alkyl-O—, and —N(R$^{15}$)$_2$, wherein each R$^{15}$ is independently selected from the group consisting of H and alkyl;

R$^6$ and R$^7$, together, form a double bond or a cycloalkyl group; and

R$^{13}$ is selected from the group consisting of H, alkyl, and —C(O)R$^{16}$, wherein R$^{16}$ is selected from the group consisting of H, —OH, alkyl, alkyl-O—, and —NR$^{17}$R$^{18}$, wherein R$^{17}$ and R$^{18}$ are each independently selected from the group consisting of H and alkyl or R$^{17}$ and R$^{18}$ together with the nitrogen atom to which they are bound, form a 5- to 6-membered heterocyclic ring.

Embodiment 2 relates to the compound of Embodiment 1 having the Formula Ia:

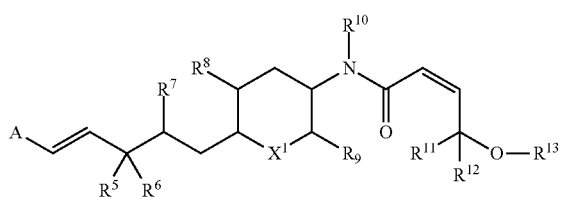

Ia or a stereoisomer, pharmaceutically acceptable salt, prodrug or antibody conjugate thereof.

Embodiment 3 relates to the compound of Embodiments 1-2 having the Formula Ib or Ic, or a stereoisomer, pharmaceutically acceptable salt, prodrug or antibody conjugate thereof:

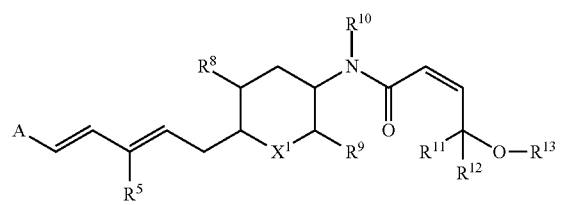

Ib

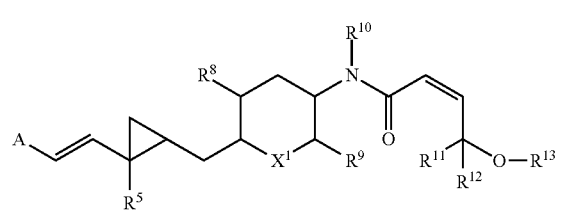

Ic

Embodiment 4 relates to the compound of Embodiments 1-3, wherein R$^{13}$ is —C(O)R$^{16}$.

Embodiment 5 relates to the compound of Embodiments 1-4, wherein R$^{16}$ is alkyl.

Embodiment 6 relates to the compound of Embodiments 1-4, wherein R$^{16}$ is —NR$^{17}$R$^{18}$.

Embodiment 7 relates to the compound of Embodiment 6, wherein R$^{17}$ and R$^{18}$ are each independently selected from the group consisting of H and alkyl.

Embodiment 8 relates to the compound of Embodiment 6, wherein R$^{17}$ and R$^{18}$ together with the nitrogen atom to which they are bound, form a 5- to 6-membered heterocyclic ring.

Embodiment 9 relates to the compound of Embodiments 1-8, wherein X$_1$ is O.

Embodiment 10 relates to a pharmaceutical composition comprising one or more of the compounds of Embodiments 1-9, or salts, prodrugs or antibody conjugates thereof, and a pharmaceutically acceptable carrier or excipient.

Embodiment 11 relates to a method of treating cancer in a subject in need of such treatment, comprising administering a therapeutically-effective amount of one or more compounds of Embodiments 1-9 or a salt, prodrug or antibody conjugate thereof or a pharmaceutical composition of Embodiment 10.

Embodiment 12 relates to the method of Embodiment 11, wherein the cancer is a solid-tumor cancer.

Embodiment 13 relates to the method of Embodiments 11-12, wherein the cancer is selected from cervical, prostate, lung, ovarian, breast, renal cell, and pancreatic cancers.

Embodiment 14 relates to the method of Embodiments 11-13 wherein a therapeutically-effective amount of the one or more compounds is administered at least twice within a 60 day period.

Embodiment 15 relates to the method of Embodiments 11-13, further comprising administering a therapeutically-effective amount of one or more compounds of Embodiments 1-9 or a salt, prodrug or antibody conjugate thereof or a pharmaceutical composition of Embodiment 10 in combination with at least one other anticancer agent.

Embodiment 16 relates to a method of making a compound of the Formula I, according to Embodiments 1-9, comprising:

contacting a compound of the Formula II:

II wherein:

A is selected from the group consisting of groups A$^1$-A$^5$:

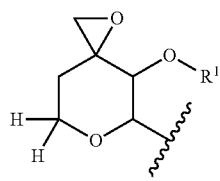

A$^1$

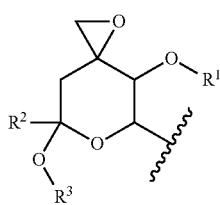

A$^2$

-continued

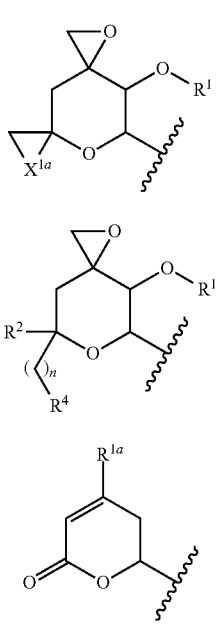

n is an integer from 1 to 10 (e.g., from 1 to 5; from 1 to 3; or from 2 to 5);

$X^{1a}$ is —$(CH_2)_g$—$X^{1b}$—, wherein g is an integer from 1 to 5 and $X^{1b}$ is a bond, O or $NR^{1a}$, wherein $R^{1a}$ is H or alkyl;

$R^1$ is selected from the group consisting of H, a hydroxyl protecting group, and alkyl;

$R^2$ and $R^3$ are each independently selected from the group consisting of H and alkyl;

$R^4$ is selected from the group consisting of —$N_3$, alkyl, aryl, heteroaryl, alkyl-$X^2$, and arylalkyl-$X^2$—, wherein $X^2$ is —O— or NH, or $R^4$ is —$C(O)R^{14}$, wherein $R^{14}$ is selected from the group consisting of H, —OH, alkyl-O—, and —$N(R^{15})_2$, wherein each $R^{15}$ is independently selected from the group consisting of H and alkyl;

with a compound of the Formula III:

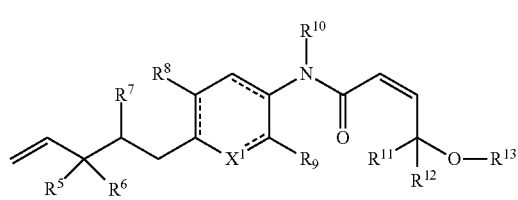

wherein:

$R^5$ and $R^8$-$R^{12}$ are each independently selected from the group consisting of H and alkyl;

$R^6$ and $R^7$, together, form a double bond or a cycloalkyl group; and $R^{13}$ is selected from the group consisting of H, alkyl, and —$C(O)R^{16}$, wherein $R^{16}$ is selected from the group consisting of H, —OH, alkyl, alkyl-O—, and —$NR^{17}R^{18}$, wherein $R^{17}$ and $R^{18}$ are each independently selected from the group consisting of H and alkyl or $R^{17}$ and $R^{18}$ together with the nitrogen atom to which they are bound, form a 5- to 6-membered heterocyclic ring.

Embodiment 17 relates to the method of Embodiment 16, wherein $R^{13}$ is —$C(O)R^{16}$.

Embodiment 18 relates to the method of Embodiments 16-17, wherein $R^{16}$ is alkyl.

Embodiment 19 relates to the method of Embodiments 16-17, wherein $R^{16}$ is —$NR^{17}R^{18}$.

Embodiment 20 relates to the method of Embodiment 19, wherein $R^{17}$ and $R^{18}$ are each independently selected from the group consisting of H and alkyl.

Embodiment 21 relates to the method of Embodiment 19, wherein $R^{17}$ and $R^{18}$ together with the nitrogen atom to which they are bound, form a 5- to 6-membered heterocyclic ring.

Embodiment 22 relates to the method of Embodiments 16-21, wherein $X_1$ is O.

The invention claimed is:

1. A compound of the formula:

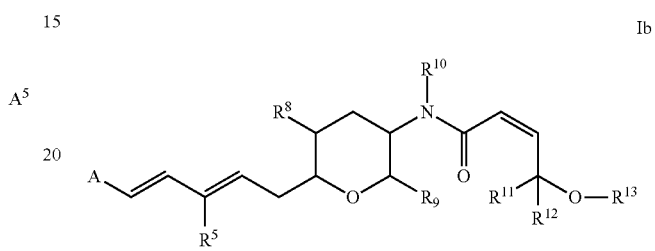

wherein
A is:

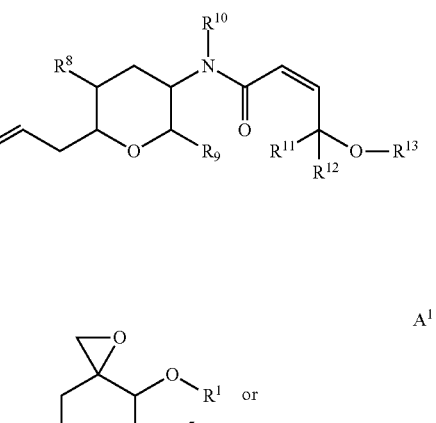

$X^{1a}$ is —$(CH_2)_g$—$X^{1b}$—, wherein g is an integer from 1 to 5 and $X^{1b}$ is a bond, O or $NR^{1a}$, wherein $R^{1a}$ is H or alkyl;

$R^1$ is selected from the group consisting of H, a hydroxyl protecting group, and alkyl;

$R^5$ and $R^8$—$R^{12}$ are each independently selected from the group consisting of H and alkyl; and $R^{13}$ is —$C(O)R^{16}$, wherein $R^{16}$ is selected from the group consisting of alkyl and —$NR^{17}R^{18}$, wherein $R^{17}$ and $R^{18}$ together with the nitrogen atom to which they are bound, form a 5- to 6- membered heterocyclic ring;

or a stereoisomer, pharmaceutically acceptable salt, prodrug or antibody conjugate thereof.

2. The compound of claim 1, wherein:
A is:

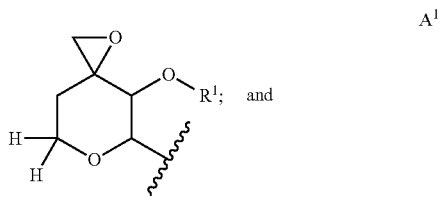

$R^{13}$ is —C(O)$R^{16}$, wherein $R^{16}$ is alkyl.

3. The compound of claim 1 wherein:
A is:

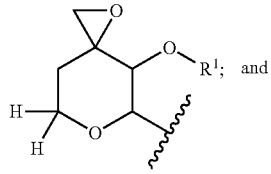

$A^1$ $R^{13}$ is —C(O)$R^{16}$, wherein $R^{16}$ is —N$R^{17}R^{18}$, wherein $R^{17}$ and $R^{18}$ together with the nitrogen atom to which they are bound, form a 5- to 6-merribered heterocyclic ring.

4. The compound of claim 1, wherein:
A is:

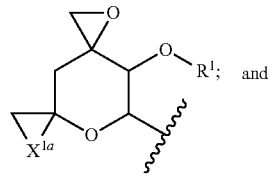

$A^3$ $R^{13}$ is —C(O)$R^{16}$, wherein $R^{16}$ is alkyl.

5. The compound of claim 4, wherein $X^{1a}$ is —(CH$_2$)$_g$—$X^{1b}$—, wherein g is 1 and $X^{1b}$ is a bond, O or N$R^{1a}$, wherein $R^{1a}$ is H or alkyl.

6. The compound of claim 5, wherein $X^{1a}$ is —(CH$_2$)—.

7. The compound of claim 1, wherein the compound of the Formula I has the formula:

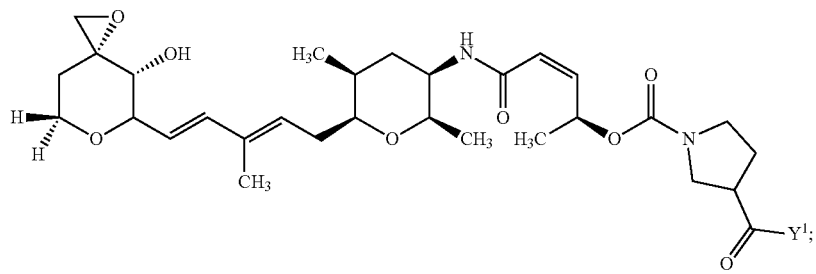

wherein $Y^1$ is selected from the group consisting of —OH, alkyl, alkyl—O—, and —N$R^{17}R^{18}$, wherein $R^{17}$ and $R^{18}$ are each independently selected from the group consisting of H and alkyl or $R^{17}$ and $R^{18}$ together with the nitrogen atom to which they are bound, form a 5- to 6-membered heterocyclic ring.

8. The compound of claim 1, wherein the compound of the Formula I has the formula:

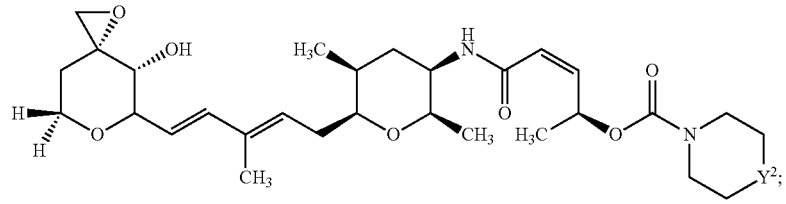

wherein $Y^2$ is nothing, such that the heterocyclic ring is a 5-membered heterocyclic ring, O, CH$_2$ or N$R^{19}$, wherein $R^{19}$ is H or alkyl.

9. A compound having the formula:

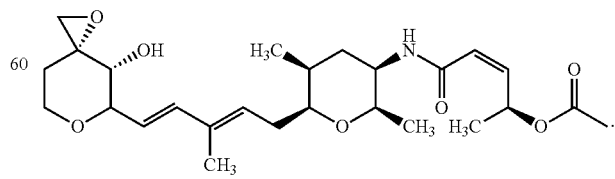

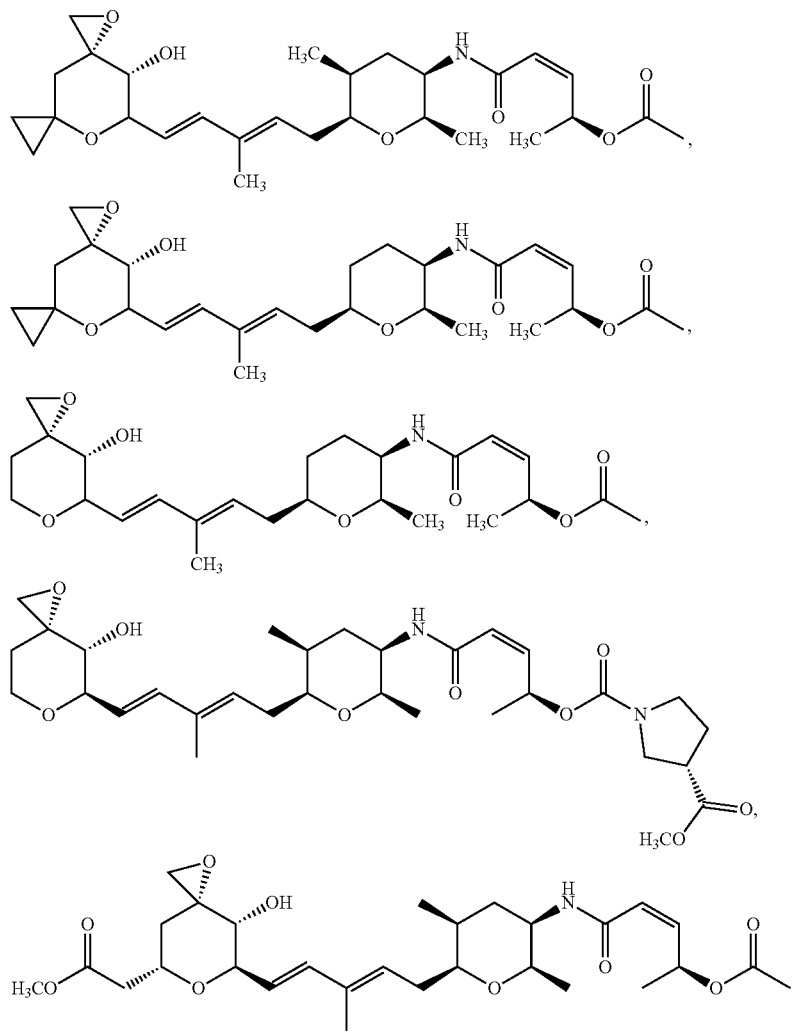

or a stereoisomer, pharmaceutically acceptable salt, prodrug or antibody conjugate thereof.

10. A pharmaceutical composition comprising one or more of the compounds of claim 1, or salts, prodrugs or antibody conjugates thereof, and a pharmaceutically acceptable carrier or excipient.

11. A method of treating cancer in a subject in need of such treatment, comprising administering a therapeutically-effective amount of one or more compounds of claim 1 or a salt, prodrug or antibody conjugate thereof.

12. The method of claim 11, wherein the cancer is a solid-tumor cancer.

13. The method of claim 11, wherein the cancer is selected from cervical, prostate, lung, ovarian, breast, renal cell, and pancreatic cancers.

14. A pharmaceutical composition comprising one or more of the compounds of claim 9, or salts, prodrugs or antibody conjugates thereof, and a pharmaceutically acceptable carrier or excipient.

15. A method for treating cancer in a subject in need of such treatment comprising administering a therapeutically-effective amount of one or more of the compounds of claim 9 in combination with at least one other anticancer agent.

16. The method of claim 15, wherein the cancer is a solid-tumor cancer.

17. The method of claim 15, wherein the cancer is selected from cervical, prostate, lung, ovarian, breast, renal cell, and pancreatic cancers.

18. The method of claim 15, further comprising administering one or more of the compounds of claim 9 in combination with at least one other anticancer agent.

* * * * *

UNITED STATES PATENT AND TRADEMARK OFFICE
CERTIFICATE OF CORRECTION

PATENT NO. : 10,858,371 B2  
APPLICATION NO. : 16/335378  
DATED : December 8, 2020  
INVENTOR(S) : Arun K. Ghosh Page 1 of 1

It is certified that error appears in the above-identified patent and that said Letters Patent is hereby corrected as shown below:

In the Specification

In Column 1, Lines 15-20, delete "STATEMENT OF U.S. GOVERNMENT SUPPORT This invention was made with government support under GM053386 awarded by the National Institutes of Health. The government has certain rights in the invention." therefor Signed and Sealed this  
Twenty-second Day of June, 2021

Drew Hirshfeld  
*Performing the Functions and Duties of the*  
*Under Secretary of Commerce for Intellectual Property and*  
*Director of the United States Patent and Trademark Office*